United States Patent [19]

Cook et al.

[11] Patent Number: 5,019,571
[45] Date of Patent: May 28, 1991

[54] 1-CARBACEPHALOSPORIN ANTIBIOTICS

[75] Inventors: Gwendolyn K. Cook; John H. McDonald, III, both of Indianapolis, Ind.

[73] Assignee: Eli Lilly and Company, Indianapolis, Ind.

[21] Appl. No.: 428,452

[22] Filed: Oct. 30, 1989

Related U.S. Application Data

[63] Continuation of Ser. No. 147,471, Jan. 25, 1988, abandoned.

[51] Int. Cl.$^5$ .................. C07D 471/04; C07D 473/00; A61K 31/435; A61K 31/47
[52] U.S. Cl. ...................................... 514/210; 540/205
[58] Field of Search ......................... 540/205; 514/210

[56] References Cited

U.S. PATENT DOCUMENTS

| | | | |
|---|---|---|---|
| 4,013,651 | 3/1977 | Spitzer | 260/243 |
| 4,396,619 | 8/1983 | Lunn et al. | 424/246 |
| 4,396,620 | 8/1983 | Lunn | 424/246 |
| 4,486,586 | 12/1094 | Narita et al. | 544/22 |
| 4,558,124 | 12/1985 | Corfield et al. | 544/22 |
| 4,665,065 | 5/1987 | Miyake et al. | 514/202 |
| 4,665,171 | 5/1987 | Evans et al. | 540/364 |
| 4,673,737 | 6/1987 | Evans et al. | 540/205 |

FOREIGN PATENT DOCUMENTS 1455016  11/1976  United Kingdom .

OTHER PUBLICATIONS

Merck Index, 1989, (11th Edition) p. 304.
*Chemical Abstracts* 106, 32696e (1986).

*Primary Examiner*—Mark L. Berch
*Attorney, Agent, or Firm*—James J. Sales; Leroy Whitaker

[57] ABSTRACT

This invention relates to antibacterial compounds of the formula

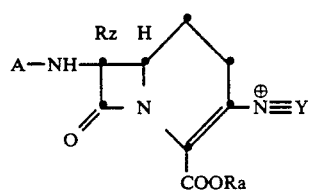

wherein A is hydrogen or an acyl group

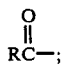

$R_a$ is a negative charge; $R_z$ is hydrogen, $C_1$–$C_4$ alkoxy, $C_1$–$C_4$ alkylthio, or a formamido group, —NHCHO; and —N$^\oplus$≡Y is a quarternary ammonium group that may be acyclic, cyclic, or a combination of the two, and may contain on or more additional hetero atoms selected from nitrogen, sulfur and oxygen; and pharmaceutically acceptable non-toxic salts thereof.

18 Claims, No Drawings

1-CARBACEPHALOSPORIN ANTIBIOTICS

This application is a continuation of application Ser. No. 07/147,471, filed on Jan. 25, 1988, now abandoned.

BACKGROUND OF THE INVENTION

This invention relates to 1-carba(dethia)cephalosporin antibiotics, intermediates for the preparation thereof, to pharmaceutical formulations comprising the antibiotics, and to a method for the treatment of infectious diseases in man and animals.

The 1-carba(dethia)cephalosporin antibiotics have the bicyclic ring system represented by the following formula wherein the numbering system is that commonly employed in the arbitrary cepham nomenclature system.

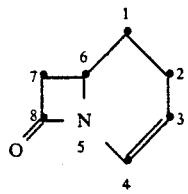

The 1-carba(1-dethia)cephalosporins are referred to herein for convenience as 1-carbacephalosporins or as 1-carba-3-cephem-4-carboxylic acids or numbered derivatives thereof. Alternatively, the compounds are 3,7disubstituted derivatives of 2-carboxy-8-oxo-1-azabicyclo[4.2.0]oct-2-enes.

The preparation of 1-carbacephalosporins and C-3 substituted methyl derivatives thereof is taught broadly by Christensen et al., in U.S. Pat. No. 4,226,866. Hirata et al., in U.K. patent application No. 2041923, teach a method for preparing 3-H and 3-halo 1-carbacephalosporins, while Hatanaka et al., *Tetrahedron Letters*, 24, No. 44, pp. 4837–4838 (1983), teach a method for preparing a 3-hydroxy-(±)-1-carbacephalosporin. A variety of 3-hydroxy-1-carbacephalosporins are also provided in EPO Patent Application Publication 209,352 while their 3-triflate (3-trifluoromethanesulfonic acid) esters are disclosed in EPO Patent Application Publication 211,540.

Although many safe and potent antibiotics of the β-lactam class are known and used clinically, the research into this class continues in an effort to find antibiotics with improved efficacy, particularly against microorganisms insensitive or resistant to the known antibiotics.

SUMMARY

7β-Acylamino-1-carba-3-cephem-4-carboxylic acids substituted in the 3-position by a quaternary ammonium group, and esters, solvates, and salts thereof, are broad spectrum antimicrobial compounds. The invention comprises formulations of the 1-carbacephalosporins useful in a therapeutic method for the treatment of infectious diseases of man and animals caused by gram-positive and gram-negative bacteria.

DETAILED DESCRIPTION

The 1-carbacephalosporins provided by this invention are represented by the formula I

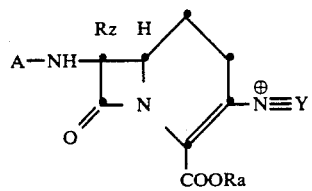

wherein A is hydrogen, an amino-protecting group, or an acyl group

wherein R is hydrogen, $C_1-C_6$ alkyl, $C_1-C_6$ alkyl substituted by cyano, carboxy, halogen, amino, $C_1-C_4$ alkoxy, $C_1-C_4$ alkylthio, trifluoromethyl, or trifluoromethylthio, naphthyl, an optionally substituted phenyl group represented by the formula

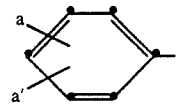

wherein a and a' independently are hydrogen, halogen, hydroxy, $C_1-C_4$ alkoxy, $C_1-C_4$ alkanoyloxy, $C_1-C_4$ alkyl, $C_1-C_4$ alkylthio, amino, $C_1-C_4$ alkanoylamino, $C_1-C_4$ alkylsulfonylamino, carboxy, carbamoyl, hydroxymethyl, aminomethyl, or carboxymethyl;

a group represented by the formula

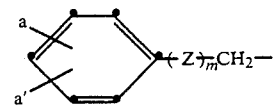

wherein a and a' have the same meanings as defined above, Z is O or S, and m is 0 or 1;

a heteroarylmethyl group represented by the formula

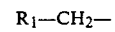

wherein $R_1$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_1-C_4$ alkyl, $C_1-C_4$ alkoxy, $C_1-C_4$ alkylsulfonylamino;

a substituted methyl group represented by the formula

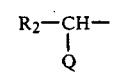

wherein $R_2$ is cyclohex 2-1,4-dienyl, or an optionally substituted phenyl group represented by the formula

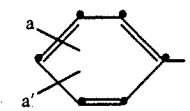

wherein a and a' have the above defined meanings or R₂ is R₁ as defined above, and Q is hydroxy, C₁-C₄ alkanoyloxy, carboxy, sulfo, amino, or a substituted amino group represented by the formula

wherein R" is C₁-C₄ alkyl, furyl, thienyl, phenyl, halophenyl, nitrophenyl, styryl, halostyryl, nitrostyryl or a group

wherein each R' is independently hydrogen or C₁-C₃ alkyl, and R''' is hydrogen, C₁-C₃ alkylsulfonyl, C₁-C₃ alkyl, or C₁-C₄ alkanoyl; or Q is a substituted amino group represented by the formula

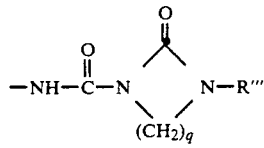

wherein R''' has the same meaning as defined above and q is 2 or 3;
or Q is a substituted amino group represented by the formula

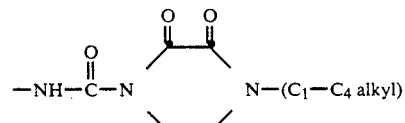

or a benzamido group represented by the formula

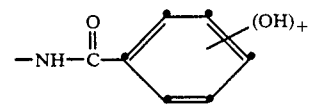

wherein t is 1 to 3:
a pyridone group

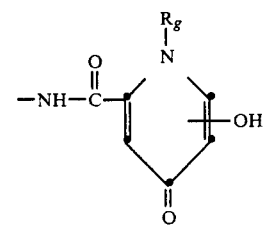

a pyridyl group

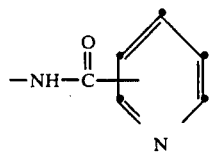

or said pyridyl group substituted by C₁-C₄ alkyl, amino, carboxy, hydroxy or halogen; an imidazolyl or pyrazolyl group

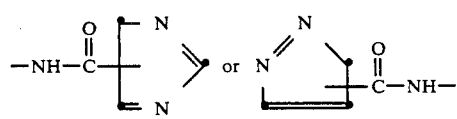

or said imidazolyl or pyrazolyl rings substituted by C₁-C₄ alkyl, carboxy, amino, or halogen;
a benzpyridazin-4-one group or tautomer thereof

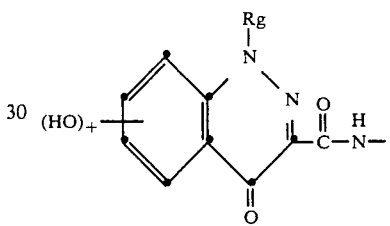

wherein Rg is hydrogen or C₁-C₃ alkyl, and t is 1 to 3; or a benzpyranone group

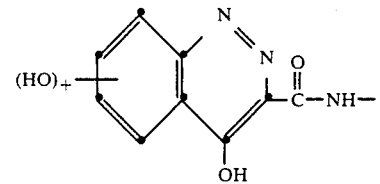

or R is a keto group or an oximino-substituted group represented by the formulae

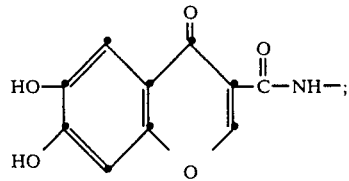

wherein R₃ is R₁ as defined above and R₄ is hydrogen, C₁-C₄ alkyl, or a carboxy-substituted alkyl or cycloalkyl group represented by the formula

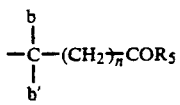

wherein b and b' independently are hydrogen or $C_1$-$C_3$ alkyl, or b and b', when taken together with the carbon to which they are bonded, form a 3- to 6-membered carbocyclic ring, n is 0-3, and $R_5$ is hydroxy, $C_1$-$C_4$ alkoxy, amino, $C_1$-$C_4$ alkylamino, or di($C_1$-$C_4$ alkyl)amino;

$R_a$ is a negative charge, hydrogen, a biologically labile group, or a carboxy-protecting group;

$R_z$ is hydrogen, $C_1$-$C_4$ alkoxy, $C_1$-$C_4$ alkylthio, or a formamido group, —NHCHO; i —N≡Y is a quaternary ammonium group that may be acyclic, cyclic, or a combination of the two, and may contain one or more additional hetero atoms selected from nitrogen, sulfur and oxygen; and solvates and pharmaceutically acceptable salts thereof.

The compounds represented by the formula I wherein A is an acyl group, RCO, and $R_a$ is hydrogen, and the pharmaceutically acceptable salts thereof, inhibit the growth of microorganisms pathogenic to man and animals. The compounds which are protected (A =an amino protecting group), deprotected (A =hydrogen), or are in esterified form ($R_a$=carboxy-protecting group) are useful as intermediates as described hereinafter.

In the above definition of the compounds represented by the formula I, "$C_1$-$C_6$ alkyl" refers to the straight and branched chain alkyl groups such as methyl, ethyl, n-propyl, isopropyl, n-butyl, t-butyl, n-pentyl, n-hexyl, 3-methylpentyl, and like alkyl groups; "$C_1$-$C_6$ alkyl substituted by cyano" refers to cyanomethyl, cyanoethyl, 4-cyanobutyl, and the like; "$C_1$-$C_6$ alkyl substituted by ... carboxy" refers to such groups as carboxymethyl, 2-carboxyethyl, 2-carboxypropyl, 4carboxybutyl, carboxybutyl, 5-carboxypentyl, and the like; "$C_1$-$C_6$ alkyl substituted by ... halogen" refers to chloromethyl, bromomethyl, 2-chloroethyl, 1-bromoethyl, 4 TM chlorobutyl, 4-bromopentyl, 6-chlorohexyl, 4-fluorobutyl, 3-fluoropropyl, fluoromethyl, and the like; "$C_1$-$C_6$ alkyl substituted by ... amino" refers to such groups as 2-aminoethyl, aminomethyl, 3-aminopropyl and 4-aminobutyl; "$C_1$-$C_6$ alkyl substituted by . . . $C_1$-$C_4$ alkoxy" refers to methoxymethyl, 2-methoxyethyl, 2ethoxyethyl, ethoxymethyl, 3-propoxypropyl, 3-ethoxybutyl, 4-t-butyloxybutyl, 3-methoxypentyl, 6-methoxyhexyl, and like group; "$C_1$-$C_6$ alkyl substituted by ... Cphd 1-$C_4$-alkylthio" refers to such groups as for example methylthiomethyl, 2-methylthioethyl, 2-ethylthiopropyl, 4-methylthiobutyl, 5-ethylthiohexyl, 3-tbutylthiopropyl, and like groups; "$C_1$-$C_6$ alkyl substituted by ... trifluoromethyl" is exemplified by 2,2,2-trifluoroethyl, 3,3,3-trifluoropropyl, 4,4,4trifluorobutyl, and the like; and "$C_1$-$C_6$ alkyl substituted by ... trifluoromethylthio" refers to, for example, trifluoromethylthiomethyl, 2-trifluoromethyl thioethyl,2-trifluoromethylthiopropyl, 4-trifluoromethylthiobutyl, 5-trifluoromethylthiohexyl, and like $C_1$-$C_6$ alkyl substituted groups.

The terms "halo" and "halogen" refer to the fluoro, chloro, bromo or iodo groups.

When, in the formula I, R is a substituted phenyl group wherein the substituent(s) are represented by a and a', examples of such groups are halophenyl such as 4-chlorophenyl, 3-bromophenyl, 2-fluorophenyl, 2,4dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3methylphenyl, and 3,5-dimethylphenyl; alkylthiophenyl such as 4-methylthiophenyl, 3-n-butylthiophenyl, 2ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylaminophenyl such as 2-acetylaminophenyl, 4-acetylaminophenyl, 3-propionylaminophenyl, and 4-butyrylaminophenyl; alkylsulfonylaminophenyl such a 3-methylsulfonylaminophenyl, 4-methylsulfonylaminophenyl, 3,5-(dimethylsulfonylamino)phenyl, 4-n-butylsulfonylaminophenyl, and 3-ethylsulfonyl aminophenyl; carboxyphenyl such as 2-, 3-, or 4-carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3aminomethylphenyl; and carboxyphenyl such as 2 TM carboxymethylphenyl, 4-carboxymethylphenyl, and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl4-fluorophenyl, 2-acetoxy-4-aminophenyl, 4-acetoxy-3-isopropylthio-4-chlorophenyl, 2-methyl-thio-4-hydroxymethylphenyl, 4-carboxy-3-hydroxyphenyl, 4-ethoxy-3-hydroxyphenyl, 4-methylsulfonylamino-2carboxyphenyl, 4-amino-3-chlorophenyl, and 2-carboxy-methyl-4-hydroxyphenyl.

Examples of RCO— groups of the formula I wherein R is a group representd by the formula

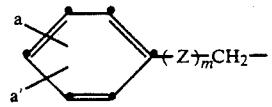

with m =0 are: phenylacetyl, 4-hydroxyphenylacetyl, 4-chlorophenylacetyl, 3,4-dichlorophenylacetyl, X-7126 - 13 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m =1 and Z =0, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m =1 and Z =S, phenylthioacetyl, 4-chlorophenylthioacetyl, 3,4dichlorophenylthioacetyl, 2-fluorophenylthioacetyl, 3-hydroxyphenylthioacetyl, and 4-ethoxyphenylthioacetyl.

Examples of $R_1$—$CH_2CO$— groups of the formula I wherein $R_1$ is a heteroaryl group are: 2-thienylacetyl, 3-thienylacetyl, 2-furylacetyl, 2-benzothienylacetyl, 2-benzofurylacetyl, indol-2-ylacetyl, 1H-tetrazol-1ylacetyl, oxazol-2-ylacetyl, oxazol-4-ylacetyl, thiazol4-ylacetyl, 2-aminothiazol-4-ylacetyl, 1,3,4-oxadiazol2-ylacetyl, 1,3,4-thiadiazol-2-ylacetyl, 5-ethyl-1,3,4-thiadiazol-2-ylacetyl, and like heteroaryl groups optionally substituted by amino, $C_1$-$C_4$ alkylsulfonylamino, hydroxy, halo, $C_1$-$C_4$ alkyl or $C_1$-$C_4$ alkoxy groups.

Examples of RCO- groups of the formula I compounds wherein R is a substituted methyl group represented by the formula $R_2$—CH(Q)- and Q is amino, carboxy, hydroxy, or sulfo, are 2-carboxy-2-phenylacetyl, 2-amino-2-(2-naphthalenyl)acetyl, 2-carboxy-2-(4-hydroxyphenyl)acetyl, 2-amino-2-phenylacetyl, 2-amino-2-(4hydroxyphenyl)acetyl, X-7126 - 14 phenyl)acetyl, 2-amino-2-(cyclohex-14-dien-1-yl)acetyl, 2-hydroxy-2-phenylacetly, 2-formyloxy-2-phenylacetyl, 2-sulfo-2-phenylacetyl, 2-sulfo-2-(4-methylphenyl)acetyl, and 2-acetoxy-2-(3-hy-droxyphenyl)acetyl, 2-amino-2-(2thienyl)acetyl, 2-amino-2-(3-benzothienyl)acetyl, 2-amino-2-(lH-tetrazol-1-yl)acetyl 2-hydroxy-2-(1,3,4-thiadiazol-2-yl)acetyl, 2-amino-2-(2-aminothiazol yl)acetyl, 2-carboxy-2-(2-thienyl)acetyl, 2-carboxy-2-(benzothien-2-yl)acetyl, and 2-hydroxy-2-yl)acetyl; and when Q is a substituted amino group represented by the formula

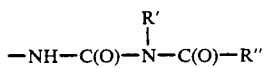

examples of such acyl groups are 2-(N-methyl-N-benzoyl-carbamoylamino)-2-phenylacetyl, 2-(N-methyl-N-cinnamoyl-carbamoylamino)-2-(2-furyl)acetyl, 2-(N,N-dimethylcarb-amoylureido)-2-(4-chlorophenyl)acetyl, 2-[N-methyl- 0 N-(2-chlorocinnamoyl)carbamoylamino]-2-(2-thienyl)acetyl, and 2-(N-ethyl-N-acetylcarbamoylamino)-2-(4-hydroxyphenyl)acetyl; and when Q is a substituted amino group represented by the formula

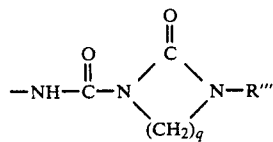

examples of acyl group RCO- are 2 TM [(3-methylimidazolidin2-one-1-yl)carbonylamino]-2-phenylacetyl, 2-[(3-acetylimi-dazolidin-2-one-1-yl)carbonylamino]-2 2-[(3-methylsulfonylim:idazolidin-2-one-1-yl)-2(2-thienyl)acetyl, and 2-[(3-acetylhexahydropyrimidin-2-one-1-yl)carbonylamino]-2-phenylacetyl; and when Q hydroxy-substituted benzamido group represented by the formula

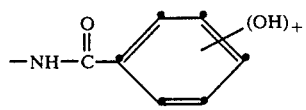

examples of such acyl groups are 2-(2,4-dihydroxybenzamido)2-phenylacetyl, 2-(4-hydroxybenzamido)-2-2-(3,4-dihydroxybenzamido)-2-(2-aminothiazol-4-yl)acety 2-(3,5-dihydroxybenzamido)-2-(3-thienyl)acetyl, and 2-(2-hydroxybenzamido)-2-(2-benzofuryl)acetyl.

Examples of RCO acyl groups of the compounds represented by formula I when R is a keto group or an oximino-substituted group represented by the formulae

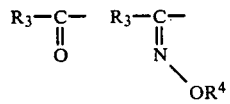

are the keto groups 2-oxo-2-phenylacetyl, 2-oxo-2-(2thienyl)acetyl, 2-oxo-2-(2-aminothiazol-4-yl)acetyl; and oximino-substituted groups 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)iminoacetyl, 2-(2-amino-1,2,4-thiadiazol-4-yl)-2-methoxyiminoacetyl, chlorothiazol-4-yl)-2-methoxyiminoacetyl, 2-(2-amino-thiazol-4-yl)-2-(2-carboxyprop-2-yl)oxyimi (2-aminothiazol-4--Yl)-2-(2-carbamoylprop-2-yl)oxyiminoacetyl, and 2-(5-amino-1,3,4-thiadiazol-2-yl)-2-methoxyiminoacetyl.

The term "carboxy-protecting group" as used in this specification refers to one of the ester derivatives of the carboxylic acid group commonly employed to block or protect the carboxylic acid group while reactions are carried out on other functional groups on the compound. Examples of such carboxylic acid protecting groups include benzyl, 4-nitrobenzyl, 4-methoxybenzyl, 3,4-dimethoxybenzyl, 2,4-dimethoxybenzyl, 2,4,6-trimethoxybenzyl, 2,4,6trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'dimethoxytrityl, 4,4',4''-trimethoxytrityl, 2-phenylprop2 T-M yl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4nitrobenzylsulfonylethyl, allyl, cinnamyl, 1-(trimethylsilylmethyl) prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. In particular, it is important not to subject the carboxy-protected 1-carbacephalosporin molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Preferred carboxylic acid protecting groups are the benzhydryl and allyl groups. Carboxy-protecting groups similar to those used in the cephalosporin, penicillin and peptide arts can also be used to protect a carboxy group substituents of the compounds provided herein. Further examples of these groups are found in E. Haslam, "Protective Groups in Organic Chemistry", J.G.W. McOmie, Ed., Plenum Press, New York, N.Y., 1973, Chapter 5, and T.W. Greene, "Protective Groups in Organic Synthesis", John Wiley and Sons, New York, N.Y., 1981, Chapter 5. A related term is "protected carboxy", which refers to a carboxy group substituted with one of the above carboxy-protecting groups.

The term "amino-protecting group" as used in the specification refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4- c methoxybenzyloxycarbonyl, 4-fluorobenzyloxycarbonyl, 4-chlorobenzyloxycarbonyl, 3-chlorobenzyloxycarbonyl, X-7126 - 18 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)iso-propoxycarbonyl, 1,1-diphenyleth-1-yloxycarbonyl, 1,1-diphenylprop-1-yloxycarbonyl, 2-phenylprop2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2- 0 (triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-en-3-yloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the 1,2-bis(dimethylsilyl)ethylene (See, e.g., U.S. Pat. No. 4,558,124), benzyloxycarbonyl, p-nitrobenzyloxycarbonyl, allyloxycarbonyl, t-butoxycarbonyl, and trityl groups. Similar amino-protecting groups used in the cephalosporin, penicillin and peptide art are also embraced by the above terms. Further examples of groups referred to by the above terms are described by J.W. Barton, "Protective Groups In Organic Chemistry", J.G.W. McOmie, Ed., Plenum Press, New York, N.Y., 1973, Chapter 2, and T.W. Greene, "Protective Groups in Organic Synthesis", John Wiley and Sons, New York, N.Y., 1981, Chapter 7. The related term "protected amino" defines an amino group substituted with an amino-protecting group discussed above.

The 1-carbacephalosporins provided herein can be esterified with a biologically labile group to form esters which form the free acid antibiotic form in vivo. When in the formula I $R_a$ is a biologically labile ester, $R_a$ is an acyloxymethyl group represented by the formula

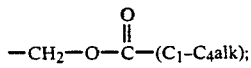

an acyloxyalkyl group represented by the formula

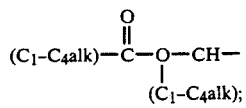

a dialkyl ether group represented by the formula $(C_2-C_4alk)-O-CH_2CH_2-O-CH_2-$;

indanyl, or the 5-methyl-2-oxo-1,3-dioxolen4-methyl-4'-ylcyclocarbonate group represented by the formula

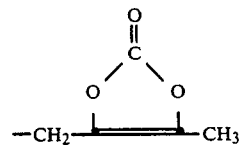

Examples of acyloxymethyl groups, $R_a$, are acetoxymethyl, propionoxymethyl and pivaloyloxymethyl. Acyloxyalkyl groups are exemplified by 1-acetoxyethyl, 1-acetoxypropyl, and 1-propionoxybutyl. Examples of dialkyl ether ester groups are β-methoxyethoxymethyl, β-ethoxyethoxymethyl, and β-t-butyloxyethoxymethyl.

The biologically labile esters of the 1carbacephalosporins can be used as pro-drugs and can provide ease of formulation and administration of the antibiotic.

Examples of acyclic, cyclic and acyclic/cyclic quaternary ammonium groups ($-\oplus=Y$) are found in columns 7, 8, 9, 10 and 36 through 52 of Y. Narita et al., U.S. Pat. No. 4,486,586 ("'586 patent"), issued Dec. 4, 1984, herein incorporated by reference. In part of the incorporated columns (10 and 36 through 52), the quaternary ammonium groups are exemplified as substituents at the 3-position of a prop-1-en-1-yl group, which group is in turn bonded to the 3-position of a cephalosporin ring.

Preferred quaternary ammonium groups of this invention are:
a) a pyridinium ring, which may be substituted with one or two of the following substituents: $C_1$ to $C_6$ alkyl, $C_1$ to $C_6$ substituted alkyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, halo, cyano, hydroxy, protected hydroxy, $C_1$ to $C_4$ alkoxy, $C_1$ to $C_4$ alkylthio, $C_1$ to $C_4$ alkylsulfoxide, $C_1$ to $C_4$ alkylsulfonyl, phenyl, substituted phenyl, formyl, $C_2$ to $C_4$ alkanoyl, benzyl, benzoyl, amino, protected amino, $C_1$ to $C_4$ pl alkylamino, di($C_1$ to $C_4$ alkyl) amino, trifluoromethyl, carboxy, protected carboxy, $C_1$ to $C_4$ alkoxycarbonyl, aminomethyl, protected aminomethyl, carboxymethyl, protected carboxymethyl, carbamoyl, which may be substituted once or twice with a $C_1$ to $C_6$ alkyl group, an aminosulfonyl group (which may be substituted once or twice with a $C_1$ to $C_6$ alkyl group), a sulfonic acid, or a substituted or unsubstituted cyclic $C_2$ to $C_{10}$ akkylene or heteroalkylene group;
b) a quinolinium, isoquinolinium, (1or 2)-pyradizinium, (1 or 3)-pyrimidinium, pyrazinium, $N^3$-($C_1$-$C_4$ allyl)imidazolinium, pyridazinium, phthalazinium, quinazolinium, purinium, thiazolinium, isothiazolinium, oxazolinium, isoxazolinium, (3 or 4)-1,3,4-thiadiazolinium, (2 or 4) 1,2,4-thiadiazolinium, (2 or 5)-1,2,5 thiadiazolinium, (3 or 4)-1,3,4-oxadiaolinium, (2 or 4)-1,2,4-oxadiazolinium, or a (2 or 5)-1,2,5-oxadiazolinium ring, or the mono or di-substituted derivatives thereof, wherein the substituents can be the same or different (and in the case of the quinolinium or isoquinolinium rings, on one or both rings) and are amino, protected amino, $C_1$ to $C_4$ alkylamino, di($C_1$ to $C_4$ alkyl)amino, hydroxy, protected hydroxy, $C_1$ to $C_4$ alkoxy, $C_1$ to $C_4$ alkylthio, $C_1$ to $C_4$ alkylsulfoxide, $C_1$ to $C_4$ alkylsulfonyl, cyano, halo, $C_1$ to $C_6$ alkyl, $C_1$ to $C_6$ substituted alkyl, trifluoromethyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, sulfonic acid, carboxy, protected carboxy, $C_1$ to $C_4$ alkoxy-carbonyl, hydroxy-($C_1$ to $C_3$ alkyl), protected hydroxy-($C_1$ to $C_3$ alkyl), formyl, $C_2$ to $C_4$ alkanoyl, an amino-sulfonyl group (which may be substituted once or twice with a $C_1$ to $C_6$ alkyl group), carbamoyl (which may be substituted once or twice with a $C_1$ to $C_6$ alkyl group), aminomethyl, protected amino-methyl, carboxymethyl, (protected carboxy)methyl, phenyl, substituted phenyl, benzoyl or benzyl;

c) a group of the formula

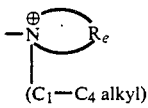

($C_1$—$C_4$ alkyl)

wherein $R_e$ together with the nitrogen atom to which it is attached form a saturated or partially unsaturated 4 to 10 membered heterocyclic ring which may contain one or more further heteroatoms selected from oxygen, nitrogen or sulfur and wherein the substituent may be $C_1$ to $C_6$ alkyl, $C_1$ to $C_6$ substituted alkyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, halo, cyano, hydroxy, protected hydroxy, $C_1$ to $C_4$ alkoxy, $C_1$ to $C_4$ *alkylthio*, $C_1$ to $C_4$ alkylsulfoxide, $C_1$ to $C_4$ alkylsulfonyl, phenyl, substituted phenyl, formyl, $C_2$ to $C_4$ alkanoyl, benzyl, benzoyl, amino, protected amino, $C_1$ to $C_4$ alkylamino, di($C_1$ to $C_4$ alkyl)amino, trifluoromethyl, carboxy, protected carboxy, $C_1$ to $C_4$ alkoxycarbonyl, aminomethyl, protected aminomethyl, carboxymethyl, protected carboxymethyl, carbamoyl (which may be substituted once or twice with a $C_1$ to $C_6$ alkyl group), aminosulfonyl (which may be substituted once or twice with a $C_1$ to $C_6$ alkyl group), or sulfonic acid, or the benzo-fused analogs of the substituted or unsubstituted, saturated or partially unsaturated ring, or d) —N⊕≡Y is tri($C_1$–$C_4$ alkyl) ammonium.

Certain of the terms describing the substituents for the above preferred quaternary ammonium groups have already been defined. Specifically, the terms "$C_1$ to $C_6$ alkyl", "$C_1$ to $C_6$ substituted alkyl", "substituted phenyl", "halo", "$C_1$ to $C_4$ alkoxy", "protected carboxy", "protected hydroxy", and "protected amino" are as defined above for Formula I.

The substituent term "$C_3$ to $C_7$ cycloalkyl" includes the cyclopropyl, cyclobutyl, cyclopentyl, cyclohexyl or cycloheptyl rings. The substituent term "$C_3$ to $C_7$ substituted cycloalkyl" indicates the above cycloalkyl rings substituted by a halogen, hydroxy, protected hydroxy, $C_1$ to $C_6$ alkyl, $C_1$ to $C_4$ alkoxy, carboxy, protected carboxy, amino, or protected amino. The substituent term "$C_5$ to $C_7$ cycloalkenyl" indicates a 1, 2, or 3-cyclopentenyl ring, a 1, 2, 3 or 4-cyclohexenyl ring or a 1, 2, 3, 4 or 5-cycloheptenyl ring, while the term "substituted $C_5$ to $C_7$ cycloalkenyl" denotes the above $C_5$ to $C_7$ cycloalkenyl rings substituted by a $C_1$ to $C_6$ alkyl radical.

The substituent term "$C_1$ to $C_4$ alkylamino" refers to methylamino, ethylamino, n-propylamino, n-butylamino, iso-propylamino and the like. The substituent term "di($C_1$ to $C_4$ alkyl)amino" denotes groups such as dimethylamino, diethylamino, methylethylamino, di(n-butyl)amino, di(n-propyl)amino and the like. Examples of the term "$C_2$ to $C_4$ alkanoyl group" are acetyl, n-propionyl, n-butyryl and the like. The substituent term "$C_1$ to $C_4$ alkoxycarbonyl" refers to groups such as methoxycarbonyl, ethoxycarbonyl, n-propoxycarbonyl, iso-propoxycarbonyl, n-butoxycarbonyl, t-butoxycarbonyl and the like.

The substituent term "$C_1$ to $C_4$ alkylthio" refers to sulfide groups such as methylthio, ethylthio, n-propylthio, iso-propylthio, n-butylthio, t-butylthio and like groups. The substituent term "$C_1$ to $C_4$ alkylsulfoxide" indicates sulfoxide groups such as methylsulfoxide, ethylsulfoxide, n-propylsulfoxide, isopropylsulfoxide, n-butylsulfoxide, sec-butylsulfoxide, and the like.

The term "$C_1$ to $C_4$ alkylsulfonyl" encompasses groups such as methylsulfonyl, ethylsulfonyl, n-propylsulfonyl, iso-propylsulfonyl, n-butylsulfonyl, t-butylsulfonyl, and the like.

The term "hydroxy ($C_1$ to $C_3$ alkyl)" refers to $C_1$ to $C_3$ alkyl groups substituted at any position by a hydroxy group, such as hydroxymethyl, 2-hydroxyethyl, 1-hydroxyethyl, 3-hydroxy(n-propyl), 2-hydroxy(n-propyl), 1-hydroxy(n-propyl), 1-hydroxy(iso-propyl) and the like. Similarly, the term "protected hydroxy-($C_1$ to $C_3$ alkyl)" refers to $C_1$ to $C_3$ alkyl groups substituted at any position by a protected hydroxy group. Examples of such groups are exemplified when, in the above hydroxy ($C_1$ to $C_3$ alkyl groups), the term "hydroxy" is read as "protected hydroxy".

The substituent term "substituted or unsubstituted cyclic $C_2$ to $C_{10}$ alkylene or heteroalkylene group" defines such a cyclic group bonded ("fused") to the b or c face of the pyridinium ring. The cyclic group may be saturated or contain one or two double bonds. Furthermore, the cyclic group may have one or two alkylene groups replaced by one or two oxygen, nitrogen or sulfur atoms.

The cyclic alkylene or heteroalkylene group may be substituted once or twice by substituents selected from the group consisting of the following moieties: hydroxy, protected hydroxy, carboxy, protected carboxy, $C_1$ to $C_4$ alkoxycarbonyl, formyl, $C_2$ to $C_4$ alkanoyl, $C_1$ to $C_6$ alkyl, carbamoyl, $C_1$ to $C_4$ alkoxy, $C_1$ to $C_4$ alkylthio, $C_1$ to $C_4$ alkylsulfoxide, $C_1$ to $C_4$ alkylsulfonyl, halo, amino, protected amino, hydroxymethyl or a protected hydroxymethyl.

The cyclic alkylene or heteroalkylene group fused onto the pyridinium radical can contain two to ten ring members, but it preferably contains three to five members. Examples of such saturated cyclic groups are when the pyridinium group is fused to a cyclopentano, cyclohexano or cycloheptano ring. When the cyclic groups are unsaturated, examples occur when the pyridinium ring is fused to a cyclopenteno, cyclohexeno or cycloheptano ring. Examples of fused cyclic groups which each contain one oxygen atom and one or two double bonds are when the pyridinium ring is fused to a furo, pyrano, dihydrofuro or dihydropyrano ring, and examples of cyclic groups which each have one sulfur atom and contain one or two double bonds are when the pyridinium ring is fused to a thieno, thiopyrano, dihydrothieno or dihydrothiopyrano ring. Examples of cyclic groups which contain two heteroatoms selected from sulfur and nitrogen and one or two double bonds are a pyridinium ring fused to a thiazolo, isothiazolo, dihydrothiazolo or dihydroisothiazolo ring. Examples of cyclic groups which contain two heteroatoms selected from oxygen and nitrogen and one or two double bonds are when the pyridinium ring is fused to an oxazolo, isoxazolo, dihydrooxazolo or dihydroisoxazolo ring. Examples of cyclic groups which contain two nitrogen heteroatoms and one or two double bonds occur when the pyridinium ring is fused to a pyrazolo, imidazolo, dihydropyrazolo or dihydroimidazolo ring.

The b or the c side of the pyridinium group can be fused to a cyclic group with three ring members. In the case of such a cyclic group containing only one heteroatom, the position of the heteroatom can result in a [2,3], [3,2]or [3,4]fusion with the pyridinium group. When the three-membered cyclic group contains two heteroatoms, the position of the heteroatoms can be such that they result in a [4,5], [5,4], [3,4]or [4,3]fusion with the pyridinium group.

Similarly, the b or c side of the pyridinium group can be fused to a cyclic group with four ring members. Such a cyclic group containing only one heteroatom can result in a [3,2], [2,3], [3,4]or [4,3]fusion with the pyridinium group. The four membered cyclic group with two heteroatoms can result in a 4,5], [5,4], [3,4], [4,3], [5,6]or [6,5]fusion to the pyridinium group.

Examples of the bicyclic pyridinium-containing ring systems that can result when the pyridinium ring is substituted with a $C_2$ to $C_{10}$ alkylene or substituted alkylene group includes groups of the formula:

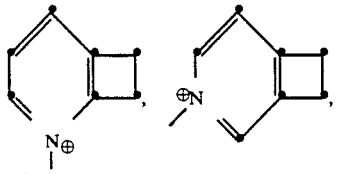

and groups such as: 5H-1-pyrindinium, 7H-1-pyrindinium, 1H-2-pyrindinium, 5H-2-pyrindinium, thieno[3,2-b]pyridinium, thieno[3,2-c]pyridinium, thieno[2,3-c]pyridinium, thieno[2,3-b]pyridinium, thieno[3,4-c]pyridinium, furo[3,2-b]pyridinium, furo[3,2-c]pyridinium, furo[2,3-b]pyridinium, furo[3,4-c]pyridinium, furo[3,4 TM b]pyridinium, oxazolo[4,5b-]pyridinium, oxazolo[5,4-b]pyridinium, oxazolo[4,5c]b]pyridinium, thiazolo[5,4-b]pyridinium, thiazolo[4,5c-]pyridinium, thiazolo[.5,4-c]pyridinium, 5,6,7,8- 0 tetrahydroquinolinium, 5,6-dihydroquinolinium, 7,8dihydroquinolinium, 5,6,7,8-tetrahydroisoquinolinium, 5,6-dihydroisoquinolinium, 7,8-dihydroisoquinolinium, 1,5-naphthyridinium, 1,6-naphthyridinium, 1,7-napthyridinium, 1,8-napthyridinium,2,6-napthyridinium, 2,7napthyridinium, 2H-pyrano[3,2-c]pyridinium, 5H-pyrano[4,3-b]pyridinium, 1 H-pyrano[3,4-b]pyridinium, 2H-pyrano[2,3-b]pyridinium, 1 H-pyrano[4,3-c]pyridinium, 1 H-pyrano[3,4-c]pyridinium, 5H-thiopyrano[4,3-b]pyridinium, 4H-thiopyrano[2,3-b]pyridinium, pyrido[3,2-d]pyrimidin5-yl, pyrido[4,3-d]pyrimidin-6-yl, pyrido[3,4-d]pyrimidin7-yl, pyrido[2,3-d]pyrimidin-8-yl, pyrido[2,3-b]pyrazin5-yl, pyrido[3,4-b]pyrazin-6-yl, pyrido[2,3-d]pyridazin- 0 1-yl, pyrido[3,4-d]pyridazin-6-yl, 4H-pyrido[2,3-d][1,3]-oxazin-8-yl, 2H-pyrido[2,3-d][1,2]oxazin-1-yl, 8H-pyrido[3,2-d][1,2]oxazin-1-yl, IH-pyrido[2,3-b][1,4]thiazin-5-yl, 3H-pyrido[2,3-b][1,4]-thiazin-5-yl, 2H-pyrid 6,7-dihydro-5H-1-pyrindinium, 6,7-dihydro-5H-2-pyrindinium, 2,3-dihydro-furo[3,2-b]pyridinium, 2,3-dihydro-furo[2,3b]pyridinium, 2,3-dihydro-thieno[2,3-b]pyridinium, 2,3-dihydro-thieno[3,2-b]pyridinium, 2,3-dihydro-thieno[2,3-c]pyridinium, the substituted derivatives thereof, and the like.

A preferred quaternary ammonium group is a substituted or unsubstituted pyridinium ring.

The substituted pyridinium ring can be substituted once or twice with the above-listed substituents. When the ring is substituted twice, the substituents may be the same or different.

Examples of a group of more particularly preferred substituents on the pyridinium ring are: 3-methyl, 4-methyl, 3-ethyl, 2-ethyl, 4-ethyl, 4-propyl, 2-(isopropyl), 3-(iso-propyl), 2-methyl, 2-(pent-3-yl), 4-(t-butyl), 2-(t-butyl), 2,4-dimethyl, 3,4-dimethyl, 3,5-dimethyl, 2,5-dimethyl, 3-ethyl-4-methyl, 3-methyl- 0 4-ethyl, 3-ethyl-6-methyl, 2-benzyl, 4-benzyl, 2-phenyl, 4-phenyl, 3-phenyl, 2-(hydroxymethyl), 3-(hydroxymethyl), 4-(hydroxymethyl), 3-hydroxy, 2-(1-hydroxyeth-1-yl), 3-(1-hydroxyeth-1-yl), 4-(1-hydroxyeth-1-yl), 3-(2-hydroxyprop-2-yl), 4-(2-hy prop-1-yl), 3-acetyl, 4-acetyl, 3-benzoyl, 4-benzoyl, 2-methylthio, 4-methylthiomethyl, 3-fluoro, 4-(N-acetamido), 3-ethoxycarbonyl, 4-ethoxycarbonyl, 3-methoxycarbonyl, 3-ethoxycarbonyl, 3- 0 carbamoyl, 4-(N-ethylcarbamoyl), 3-(N,N'-diethylcarbamoyl), 4-cyano, 4-(aminosulfonyl), 4-(potassium eth-1-yl-2-sulfonate), 4-cyclopentyl, 4-(p-chlorobenzyl), 3-alkyl, 5-hydroxy-2-methyl, 3-hydroxy-4-methyl, 4-(1hydroxypropyl), 3-(1-hydroxypropyl), 3-(2-hydroxy-2- C methylpropyl), 2-(hydroxymethyl)-4-methyl, 2-(1,3-di hydroxyprop-2-yl), 4-(2-hydroxypropyl), 4-(3-hydroxypropyl), 3-cyclohexyl, 4-cyclohexyl, 3-cyclopentyl, 4-(cyclohex-1-enyl), 3-(cyclohex-1-enyl), 4-(cyclopent1-enyl), 3-(cyclopent-1-enyl), 3-(cyclohept-1-enyl), 3-(4-methylcyclohex-1-enyl), 3-(1-hydroxycyclohexyl), 3-(1-hydroxycyclopentyl), 4-(1-hydroxycyclohexyl), 4 (1-hydroxycyclopentyl), 3-(1-hydroxycycloheptyl), 4-methoxy-3-methyl, 3-methoxy-4-methyl, 3-(is 3-propoxy, 2-(1-methoxyeth-2-yl), 4-(2-ethoxyeth-1-yl), 2-(2-ethoxyeth-1-yl), 4((acetylmethyl), 4-(3-chloropropyl), 3-(3-chloropropyl), 3-trifluoromethyl, 3-bromo-4-methyl, 3-(cyanomethyl), 4-(1-hydroxy-1-(sulfonic acid)methyl), 4-(cyclopent-2-enyl), 4-(cyclopropyl), and the various protected hydroxy analogs thereof; and a pyridinium ring substituted with the above-described $C_2$ to $C_{10}$ alkylene ring, resulting in the following bicyclic ring examples: 5,6-dihydro-5H-1-pyrindinium, 5,6,7,8-tetrahydroquinolinium, 5,6,7,8-tetrahydroisoquinolinium, 3-methyl-5,6,7,8tetrahydroquinolinium, 6,7-dihydro-5H-2-pyrindinium, 7-hydroxy-5,6-dihydro-5H-1-pyrindinium, 5,6,8,9-tetrahydro-7H-cyclohepta[b]pyridinium, 2,3-dihydr 2,3-b]pyridinium, 3-hydroxy-2,3-dihydro-furo[2,3b-]pyridinium, 3-keto-2,3-dihydro-furo[2,3-b]pyridinium, thieno[3,2-b]pyridinium, thieno[3,2-c]pyridinium, furo[3,2-c]pyridinium, 2-methylthiazolo[4,5-c]pyridinium, and 2-methylthiazolo[5,4-c]pyridinium.

A preferred group of substituted pyridinium rings are 4-carbamoylpyridinium, 4-(2-(sulfoethyl)pyridinium, 5,6-dihydro-5H-1-pyrindinium, thieno[3,2-b]pyrindinium, thieno[3,-c]pyridinium, furo[3,2-c]pyridinium, 2-methylthieno[4,5-c]pyridinium and 2-methylthieno[5,4c]pyridinium.

A more preferred group of pyridinium rings is pyridinium, 4-carbamoylpyridinium, 4-(sodium eth-1-yl-2-sulfonate)pyridinium, 5,6-dihydro-5H-1-pyrind 2-methylthiazolo[4,5-c]pyridinium and 2-methylthiazolo[5,4c]pyridinium.

Another preferred quaternary ammonium group is the substituted or unsubstituted quinolinium group. The quinolinium group may be substituted on the A or B ring or on both rings with the same or different substituents. Some examples and description of substituted quinolinium groups can be found in W.H.W. Lunn, U.S. Pat. No. 4,396,620, issued Aug. 2, 1983, herein incorporated by reference. Columns 3, 4, 13, 14, 15, 16, 17, 18, 19 and 20 of the 620 patent are particularly helpful in this regard.

A preferred group of quinolinium groups are the quinolinium, 5-aminoquinolinium, 3-aminoquinolinium, 2-aminoquinolinium, 7-aminoquinolinium, 5-hydroxyquinolinium, 6-hydroxyquinolinium and 7-hydroxyquinolinium group.

Another preferred quaternary ammonium group is the substituted or unsubstituted isoquinolinium group. The isoquinolinium ring may be substituted on the A or the B ring or on both rings with the same or different substituents.

Examples and description of substituted isoquinolinium groups can be found in W.H.W. Lunn, U.S. Pat. No. 4,396,619, issued Aug. 2, 1983, herein incorporated by reference. Columns 3, 4, 13, 14, 16, 17, 18, 19, 20, 21 and 22 of the 619 patent are particularly helpful in this regard.

A preferred group of isoquinolinium substituents are isoquinolinium, the hydroxy-substituted isoquinolinium groups such as 5-hydroxyisoquinolinium or 4-hydroxyisoquinolinium, or the amino-substituted isoquinolinium groups such as 4-aminoisoquinolinium, 5-aminoisoquinolinium or 6-aminoisoquinolinium.

A more preferred group of isoquinolinium groups are the isoquinolinium, 5-aminoisoquinolinium and 8-hydroxyisoquinolinium groups.

Another preferred quaternary ammonium group is a 1-pyridazinium or 2-pyridazinium group, or a mono- or di-substituted analog thereof, wherein the substituents can be the same or different.

A preferred group of pyridazinium substituents include: pyridazinium (unsubstituted), 3,6-dichloropyridazinium, 3-methylpyridazinium, 3,6-di(-hydroxy)pyridazinium, 3-chloro-6-methoxypyridazinium, 3,5-di(hydroxy)pyridazinium, 4-methylpyridazinium, 3-methoxypyridazinium, 4-methoxypyridazinium, 3,6-dimethylpyridazinium, 3-(methylthio)pyridazinium, 4-(methylthio)pyridazinium, 3-aminopyridazinium, 4-aminopyridazinium, 3-amino-6-methylpyridazinium, 3,6-di(methoxy)pyridazinium, 6-aminopyridazinium, 6-(methylamino)pyridazinium, 6-chloro-3-methoxypyridazinium, 5-methylpyridazinium, and 5-ethylpyridazinium.

A more preferred pyridazinium group is unsubstituted pyridazinium.

Another preferred quaternary ammonium group is a 1-pyrimidinium or 3-pyrimidinium group, or a mono- or di-substituted analog thereof, wherein the substituents can be the same or different. A preferred group of pyrimidinium substituents is 4,5-diaminopyrimidinium, 4,6-diaminopyrimidinium, the (protected amino)-pyrimidinium analogs thereof, 4-phenylpyrimidinium, 4,6dichloropyrimidinium, 2,4 TM dichloropyrimidinium, 4,6di(methyl)pyrimidinium and the unsubstituted pyrimidinium group. A more preferred pyrimidinium group is unsubstituted pyrimidinium.

Another preferred quaternary ammonium group is the pyrazinium group, or a mono- or di-substituted analog thereof, wherein the substituents can be the same or different. A preferred group of pyrazinium substituents include 3-methylpyrazinium, 3,5-di(methyl)-pyrazinium, 3-aminopyrazinium, 3-protected aminopyrazinium, 3-ethylpyrazinium, 3-(diethylamino)-pyrazinium, 3-(ethylamino)pyrazinium, 3,5-diethylpyrazinium, 3-(dimethylamino)pyrazinium, 2,6-dimethylpyrazinium, 2-chloropyrazinium, 3-chloropyrazinium, 2-aminopyrazinium, 2-carboxy-3aminopyrazinium, 2,6-dichloropyrazinium, 2,3-dimethylpyrazinium, 2,5-dimethylpyrazinium, 2-methylpyrazinium, 2-carbamoylpyrazinium, 2-carboxypyrazinium, 2,3-dicarbamoylpyrazinium, 2,3-dicarboxypyrazinium, 2methylpyrazinium, 2-ethylpyrazinium, 2-ethyl-3-methylpyrazinium, 2-ethyl-5-methylpyrazinium, 2-ethyl-6methylpyrazinium, 2,5-diethylpyrazinium, 3-(iso-propyl)2-ethoxypyrazinium, 3-(sec-butyl)-2-methoxypyrazinium and 3-(iso-butyl)-2-methoxypyrazinium. A more preferred group of pyrazinium substituents is the unsubstituted pyrazinium and the 2-(dimethylamnoi)pyrazinium-1-yl groups.

Another group of preferred quaternary ammonium substituents is the substituted or unsubstituted thiazolinium, isothiazolinium, oxazolinium, isoxazolinium, $N^3$–($C_1$–$C_4$ alkyl) imidazolinium, 1,3,4-thiadiazolinium, 1,2,4-thiadiazolinium, 1,2,5-thiadiazolinium, 1,3,4oxadiazolinium, 1,2,4-oxadiazolinium or 1,2,5-oxadiazolinium groups, each of which can be substituted once or twice with the same or different substituents. The groups containing two nitrogen atoms in the ring may be quaternized at either ring nitrogen.

A preferred ring system in this group is the substituted or unsubstituted thiazolium group. A preferred thiazolium group is the 4-methyl-5-(1-hydroxy-eth 2-yl)-thiazolium ring.

Also, a preferred quaternary ammonium group is a group of quaternary ammonium substituents which have the formula:

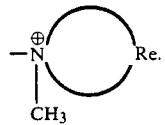

The preferred compounds of the above quaternary ammonium group occur when the variable Re, taken together with the nitrogen atom to which it is bonded, represents a saturated or mono-unsaturated 5-, 6-, 7- or 8-membered heterocyclic ring optionally containing a further nitrogen or oxygen heteroatom. The heterocyclic ring may be mono-substituted and may also be fused with a benzene ring.

A preferred substituent within this quaternary ammonium group is of the formula

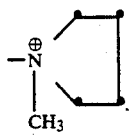

Further examples and description of this type of quaternary ammonium group can be found in P.E. Ayres, U.S. Patent No. 4,168,309, issued September 18, 1979, herein incorporated by reference.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated, with fully unsaturated rings being preferred.

Furthermore, the above optionally substituted five-membered or six-membered rings can optionally be fused to a aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heterocyclic ring": thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, di- thiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzthiazolyl, benzimidazolyl and indolyl.

A preferred group of the above heterocyclic rings are 5-membered ring systems containing a sulfur or oxygen atom and one to three nitrogen atoms. Examples of such preferred groups include thiazolyl, in particular thiazol-2-yl and thiazol-2-yl N-oxide, thiadiazolyl, in particular 1,3,4-thiadiazol-5-yl and 1,2,4-thiadiazol5-yl, oxazolyl, preferably oxazol-2-yl, and oxadiazolyl, such as 1,3,4-oxadiazol-5-yl and 1,2,4-oxadiazol-5-yl. A group of further preferred examples of 5-membered ring systems with 2 to 4 nitrogen atoms include imidazolyl, preferably imidazol-2-yl; triazolyl, preferably 1,3,4-triazol -5-yl, 1,2,3-triazol-5-yl, and 1,2,4-triazol 5-yl, and tetrazolyl, preferably 1H-tetrazol-5-yl. A preferred group of examples of benzo-fused derivatives are, in particular, benzoxazol-2-yl, benzthiazol-2-yl and benzimidazol-2-yl.

Further specific examples of the above heterocyclic ring systems are 6-membered ring systems containing one to three nitrogen atoms. Such examples include pyridyl, such as pyrid-2-yl, pyrid-3-yl and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides, and the pyridyl, pyrimid-2 TM yl, pyrimid-4-yl, pyridazinyl and the 1,3,4-triazin-2-yl radicals, are a preferred group.

The substituents for the optionally substituted heterocyclic ring systems, and further examples of the 5- and 6- membered ring systems discussed above, are found in W. Dürckheimer et al., U.S. Pat. No. 4,278,793, issued July 14, 1981, columns 9 through 21 and columns 33 through 188, herein incorporated by reference. (In columns 33 through 188, examples of the term "heterocyclic ring" are included in the heterocyclic thiomethyl groups listed under heading "A".)

A particularly preferred group of examples of the term "heterocyclic ring" is 1,3-thiazol-2-yl, 4-(carboxymethyl)-5-methyl-1,3-thiazol-2-yl, 4-(carboxymethyl)-5-methyl-1,3-thiazol-2-yl sodiu thiadiazol-5-yl, 3-methyl-1,2,4-thiadiazol-5-yl, 1,3,4- 0 triazol-5-yl, 2-methyl-1,3,4-triazol-5-yl, 2-hydroxy- 0 1,3,4-triazol-5-yl, 2-carboxy-4-methyl-1,3,4-triazol5-yl sodium salt, 2-carboxy-4-methyl-1,3 1,3-oxazol-2-yl, 1,3,4-oxadiazol-5-yl, 2-methyl-1,3,4-oxadiazol-5-yl, 2-(hydroxymethyl)-1,3, 1,2,4-oxadiazol-5-yl, 1,3,4-thiadiazol-5-yl, 2-methyl1,3,4-thiadiazol-5-yl, 2-thiol-1,3,42-(methylthio)-1,3,4-thiadiazol-5-yl, 2-amino-1,3,4- C thiadiazol-5-yl, lH-tetrazol-5-yl, 1-methyl-lH-tetrazol- 0 5-yl, 1-(1-(dimethylamino)eth-2-yl)-lH-tetrazol-5-yl, 1-(carboxymethyl)-lH-tetrazol-5-yl, 1-(carboxymethyl) X-7126 TM 39 -1H-tetrazol-5-yl sodium salt, 1-(methylsulfonic acid)-IH-tetrazol-5-yl, 1-(methylsulfonic acid)-1H-tetrazol 5-yl sodium salt, 2-methyl-1H-tetrazol-5-yl, 1,2,3- 0 triazol-5-yl, 1-methyl-1,2,3-triazol-5 TM yl, 2-methyl- 0 1,2,3-triazol-5-yl, 4-methyl-1,2,3-triazol-5-yl, pyrid-2-yl N-oxide, 6-methoxy-2-(N-oxide)-pyridaz-3-yl, 6-hydroxypyridaz-3-yl, 1-methylpyrid-2-yl, 1-methylpyrid4 TM yl, 2-hydroxypyrimid-4-yl, 1,4,5,6-tetrahydro-5,6-dioxo-4-methyl-as-triazin-3-yl, 1,4,5,6-te (formylmethyl)-5,6-dioxo-as-triazin-3-yl, 2,5-dihydro- 0 5-oxo-6-hydroxy-as-triazin-3-yl, 2,5-dihydro- 0 5-oxo-6hydroxy-as-triazin-3-yl sodium salt, 2,5-dihydro- c 5-oxo-6-hydroxy-2-methyl-as-triazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-o methyl-as-triazin-3-yl, 2,5-dihydro-5-oxo-2,6-dimethyl-as-triazin-3-yl, tetrazolo[1,5-b]pyridazin-6 8-aminotetrazolo[1,5-b]pyridazin-6-yl.

A further preferred group of 1-carbacephalosporins is represented by the formula I wherein R is the substituted methyl group

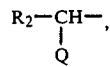

particularly those compounds wherein Q is amino or substituted amino. Especially preferred compounds are substituents, together with the CO moiety to which they are attached, are D-phenylglycyl, D-4-hydroxyphenylglycyl, D-2-thienylglycyl, D-benzothien-3-ylglycyl, and like functionalities.

A further preferred group is represented by formula I wherein R is the group

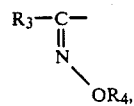

in the syn form.

Particularly preferred compounds are represented when $R_4$ is $C_1$–$C_4$ alkyl or a carboxy substituted alkyl group such as carboxymethyl, 2-carboxyethyl, 3-carboxypropyl, and 2-carboxy TM 2 TM propyl; and $R_3$ is a five or six membered heterocyclic ring $R_1$, in particular, an amino substituted heterocyclic. Especially preferred heterocyclics are the 2-aminothiazole or 2-aminooxazole ring. Examples of such preferred RCO-groups are (2-aminothiazol-4-yl)(methoxyimino)acetyl, (2-aminooxazol-4-yl)(methoxyimino)acetyl, and the like.

Further preferred compounds of this group are represented by the formula

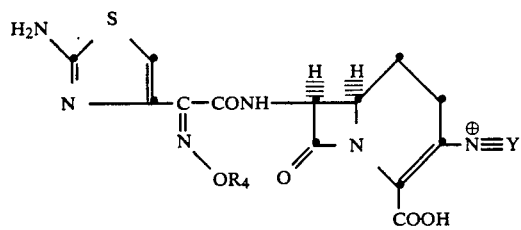

and the pharmaceutically acceptable non-toxic salts thereof. Preferred structures are those when $—N\oplus \equiv Y$ is substituted or unsubstituted pyridinium, quinolinium, isoquinolinium, 1- or 2-pyridazinium, 1- or 3-pyrimidinium, pyrazinium, imidazolinium, thiazolinium, isothiazolinium, oxazolinium, isoxazolinium, 1,2,4-, 1,2,5-, or 1,3,4-thiadiazolinium or -oxadizolinium, or a group of the formula

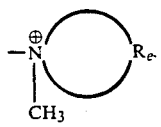

The term "pharmaceutically acceptable salt" refers to salts of the carboxy group or other acidic moiety in the molecule, such as a carboxy or sulfo substituent group, and includes salts formed with organic amines and inorganic bases. Such amines and bases include those whose counter-ions are chosen from the alkali and alkaline earth metals (such as lithium, sodium, potassium, barium and calcium); ammonium; and the organic cations (such as dibenzylammonium, benzyl-ammonium, 2-hydroxyethylammonium, bis 2-hydroxyethyl-ammonium, phenylethylbenzylammonium, dibenzylethylenediammonium, and like cartons). Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist in the presence of the quaternary ammonium group. A preferred cation for the carboxylate anion is the sodium cation.

Furthermore, the term includes salts that form by standard acid-base reactions with basic groups of the compounds of this invention (such as amino groups) and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The compounds of Formula I may also exist as solvates. Thus, these compounds may crystallize with, for example, waters of hydration, or one, a number of, or any fraction thereof of molecules of the mother liquor solvent, such as ethanol. The solvates of such compounds are included within the scope of this invention.

Furthermore, the compounds of Formula I encompass the requisite negative counter-ion of the quaternary ammonium group. Such a counter-ion may be a carboxylate anion, an anionic group bound at some other place to the molecule or a separate external counter-ion such as a halo or acyloxy anion.

The 3-quaternary ammonium compounds of this invention are prepared by reacting the corresponding 3-triflate ester with the appropriate amine $N \equiv Y$. The reaction may be performed on any of the protected or otherwise functionalized triflate esters but is preferably the last or penultimate step in a series designed to introduce the other desired fuctionalities into the molecule, such as the desired acyl group of the 7-position. Moreover, blocking groups, both on the 4-carboxy moiety and which protect any acid or amine groups on the 7-substituent, are preferably introduced before the conversion of the triflate group into the desired quaternary ammonium functionality. The blocking groups can then be removed sequentially, or in some cases, such as in a preferred embodiment in which $R_a$ is allyl and the protecting group on the 7-side chain is allyloxycarbonyl, can be removed under the same conditions. Other transformations, such as salt formation, conversion to a biological labile ester, etc., can be carried out thereafter.

A typical series of transformations is summarized in Scheme I below:

Scheme I

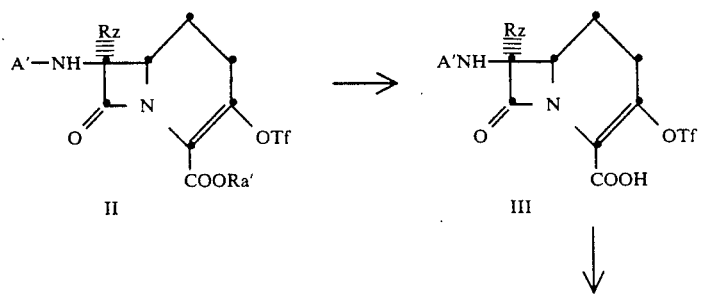

Scheme I -continued

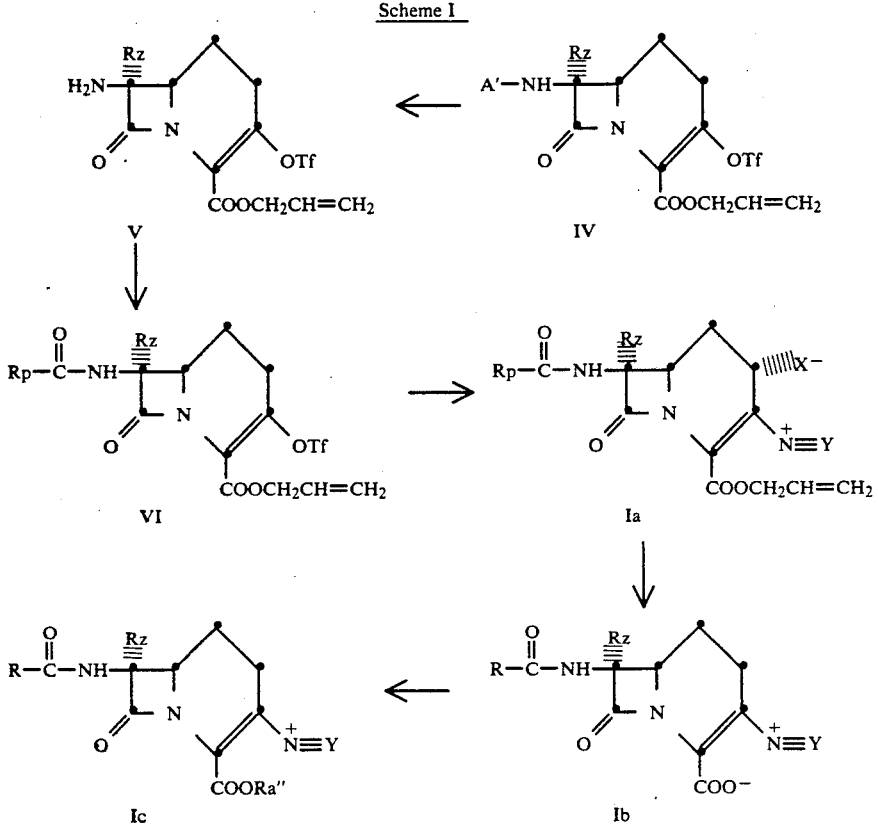

wherein A' is an amino protecting group, Tf is a triflate moiety ($-SO_2CF_3$), $R_a'$ is a carboxy protecting group, such as a p-nitrobenyl moiety, $R_p$ is R or a protected R group, and $R_a''$ is a biologically labile group.

While this scheme employs a specific acid protecting group, i.e., the allyl ester of the 4-carboxy group, it will be apparent that any other suitable protecting groups as described earlier can be employed with the corresponding changes in the deprotection step as will be appreciated by those skilled in the art.

According to Scheme I, a triflate ester of Formula II can, if necessary, be hydrolyzed to prepare the corresponding acid III and then converted to a protected ester IV which is most suitable for the subsequent transformations. Hydrolysis of the carboxy protecting group followed by protection of the carboxylic acid with another protective group can be accomplished by employing procedures that are well known in the cephalosporin, penicillin, and peptide arts.

Examples of these groups are found in T. W. Green, "Protective Groups in Organic Synthesis," John Wiley and Sons, New York, NY, 1981.

Similarly, the amino protecting group (or any other acyl group of the 7-position) on the amine of IV can be removed and replaced with the desired side chain RCO or a protected version thereof.

The transformation of the suitable substituted and protected triflate ester VI to the corresponding quaternary ammonium derivative Ia is accomplished by allowing VI to react with a molar excess of the amine N≡Y. In cases where the amine is a liquid, the reaction is best carried out by using the amine both as reactant and solvent. The reaction is carried out by simply stirring the amine and triflate ester at temperatures from approximately 0° C to about 100° C, preferably 20°-30° C.

The reaction is usually complete in 1-3 days. Alternatively, an inert solvent, such as acetonitrile, can be used in addition to the above reagents.

The quaternary ammonium compounds Ia, or other acid protected derivatives thereof, can then be deprotected to provide the carboxylic acids of this invention, Formula Ib. In certain cases, the deprotection will remove both the carboxy protecting group and a protecting group on the 7-side chain. In the preferred situation where the allyloxycarbonyl group is used to protect an amino group in the 7-position side chain or the 7-amino group, both this group and the allyl ester can be removed upon treatment with triphenyl phosphine, palladium acetate, and tributyl tin hydride in solvents such as acetonitrile and diethyl ether, as taught by O. Dangles, F. Guibe, and G. Balovoine, J. Org. Chem., 52, 4984 (1987) and L. N. Jungheim and S. K. Sigmund, J. Org. Chem., 52, 4007 (1987). Alternatively, the allyl or other ester group may be removed separately from a side chain protecting group in a sequence appropriate for the selective removal of the respective protecting groups.

If a labile ester product is desired, Ib can be transformed into the corresponding derivative Ic by standard methods.

The 7β-acylamino-7α-substituted-1-carbacephalosporins represented by the formula I wherein $R_z$ is $C_1$-$C_4$ alkoxy, or precursors thereto, are prepared according to the method described by Koppel, U.S. Pat. No. 3,994,885. The 7α-formamido substituted compounds wherein $R_z$ is —NHCHO are obtained by the method described by Millner, U.S. Pat. No. 4,539,159. According to this method, a 7β-acylamino- or 7β-protected amino-7-α-methylthio-substituted 1-carbacephalosporin is reacted with anhydrous ammonia or an ammonium salt in the presence of mercuric acetate to form the corresponding 7α-amino derivative. The latter is formylated to the 7α-formamido derivative.

The starting material II is available according to the disclosure and procedure of EPO Patent Application No. 211,540. These triflate derivatives are prepared from the corresponding 3-hydroxy compounds reported in EPO Patent Application No. 209,352. Other reagents and intermediates required for preparing the compounds of this invention are commercially available, reported in the literature, or can be prepared by conventional methods known in the art. For example, the triflate esters may be prepared from, or converted into, the corresponding 3-mesyl, -tosyl, -phosphonate, or -halo congener by standard methods. These derivatives can therefore serve as intermediates to the 3-triflates or as derivatives of the triflates which can be converted into the 3-quaternary compounds of this invention according to the methods described above for the 3-triflate intermediates.

The following examples further illustrate the preparation of the starting materials, intermediates, and compounds of this invention. The examples are illustrative only and are not intended to limit the scope of the invention in any way. The term "m/e" used in characterizing the products refers to the mass-to-charge ratio of ions which appear in the mass spectra of the products. In general, the values correspond to molecular weights of the major peaks, and are so designated "M+"Where structures were confirmed by mass spectral, infrared, or proton magnetic resonance analysis, the compound is so designated by "MS", "IR", or "NMR", respectively, in the solvent as indicated. NMR values are reported as parts per million (ppm).

EXAMPLE 1

1-[7β-{[2-(allyloxycarbonylamino)-4-thiazolyl](methoxyimino)acetyl}amino)-2-(allyloxycarbonyl)-8-oxo-1-azabicyclo[4.2.0]oct-2-en-3-yl]pyridinium trifluoromethanesulfonate A. Preparation of p-nitrobenzyl 7β-phenoxyacetyl-amino-3-trifluoromethylsulfonyloxy-1-carba(dethia)-3-cephem-4-carboxylate.

A solution of 4.59 g of p-nitrobenzyl 7β-phenoxyacetylamino-3-hydroxy-1-carba (dethia)-3-cephem 4-carboxylate in 98 ml of distilled methylene chloride was cooled to −40° C. by means of an external acetonitrile/dry ice bath. With stirring, 1.49 g of triethylamine were added followed by the rapid addition of 2.91 g of triflic anhydride. After 5 minutes, the reaction mixture was poured into a saturated aqueous sodium bicarbonate solution. The layers were separated and the organic layer was washed twice with 0.1 N hydrochloric acid, once with distilled water, then dried over magnesium sulfate, filtered, and concentrated in vacuo. Hexane was added and the mixture again evaporated in vacuo. The residue was triturated with 100 ml of hexane providing 5.5 g of the desired subtitle intermediate as light pink-/beige crystals.

m/e: M+ +1 = 600.

NMR (CDCl$_3$): 1.50–2.18 (2H, m), 2.46–2.74 (2H, m), 3.82–4.10 (1H, m), 4.50 (3H, s), 5.30–5.54 (3H, m), 6.78–7.58 (6H, m), 8.18 (2H, d).

B. Preparation of 7β-phenoxyacetylamino-3-tri-fluoromethanesulfonyloxy-1-carba (dethia)-3-cephem-4carboxyli acid.

A mixture of 5.30 g of the ester of Example 1A above, 135 ml of tetrahydrofuran, and 135 ml of dimethylformamide was cooled by means of an external ice/ethanol bath. Under a nitrogen atmosphere, 135 ml of 1N hydrochloric acid were added followed by the addition of 2.20 g of zinc powder. After stirring for two hours at 0° C., the mixture was poured into 2 liters of ethyl acetate, washed twice with 400 ml of 1N hydrochloric acid and once with 400 ml of water, dried over magnesium sulfate, filtered, and concentrated in vacuo providing 4.2 g of of the desired subtitle acid which was used in the subsequent step without further purification.

C. Preparation of allyl 7β-phenoxyacetylamino-3-trifluoromethylsulfonyloxy-1-carba (dethia)-3-cephem-4carboxyl The 4.2 g of acid intermediate from Example 1B above was suspended in 100 ml of a saturated sodium bicarbonate solution. To the suspension were added 3.19 g of tetrabutylammonium hydrogen sulfate followed by the addition of 50 ml of methylene chloride. After stirring for 10 minutes, the mixture was extracted 4 times with methylene chloride. The combined organic extracts were dried over sodium sulfate, filtered, and concentrated in vacuo. The resulting oil was dissolved in 10 ml of chloroform to which 1.307 g of allyl bromide were added. The reaction mixture was stirred under a nitrogen atmosphere overnight. The mixture was then concentrated in vacuo and chromatographed over silica gel eluting with 50:50 ethyl acetate/hexane. The appropriate fractions were combined and concentrated in vacuo, providing 3.0 g of the desired title intermediate as a clear oil.

NMR (CDCl$_3$): 1.84–2.24 (2H, m), 2.52–2.76 (2H, m), 3.76–4.12 (1H, m), 4.50 (1H, s), 4.76 (2H, 2d), 5.16–5.56 (4H, m), 5.68–6.20 (2H, m), 6.76–7.56 (6H, m).

D. Preparation of allyl 7β-amino-3-trifluoro-methylsulfonyloxy-1-carba(dethia)-3-cephem-4-carboxylate.

To a solution of 2.6 g of the allyl ester from Example 1C above in 52 ml of methylene chloride were added 0.50 g of pyridine followed by 1.21 g of phosphorus pentachloride. After stirring at room temperature for over 1 hour, an additional 0.020 g of pyridine and 0.054 g of phosphorus pentachloride were added. After stirring an additional 30 minutes, the reaction mixture was added to a solution of 3.85 g of isobutyl alcohol and 215 ml of methylene chloride which had previously been cooled to −20° C. After stirring for 90 minutes, 150 ml of water were added and the mixture stirred vigorously for 30 minutes. The layers were separated and the organic layer washed twice with 1N hydrochloric acid. The aqueous layers were combined, adjusted to pH 7.5, and extracted 4 times with chloroform. The chloroform extracts were combined, dried over sodium sulfate, filtered, and concentrated in vacuo. The resulting clear oil contained the title intermediate which was used in the subsequent acylation step without further purification.

E. Preparation of allyl 7β-({[2-(allyloxycarbonyl)-amino-4-thiazolyl](methoxyimino)acetyl}amino)-3-tri methylsulfonyloxy-1-carba(dethia)-3-cephem-4-carboxylate.

Under a nitrogen atmosphere, 1.04 g of 2-{[(allyloxycarbonyl)amino]-4-thiazolyl}(methoxyimino)acetic acid were suspended in 37 ml of methylene chloride. After cooling by means of an external ice/ethanol bath, 0.52 ,g of N-methylmorpholine were added to the reaction mixture followed by the introduction of a solution of 0.90 g of 2-chloro-4,6-dimethoxy-1,3,5-triazine in 2 ml of methylene chloride. After stirring at 0° C for 30 minutes, the reaction was stirred an additional 45 minutes at room temperature. The solution was cooled by means of the external ice/ethanol bath and the solution of the crude free amine from Example lD above in 15 ml of methylene chloride was added in dropwise fashion. After stirring at room temperature overnight, the resulting solid was removed by filtration and the filtrate concentrated in vacuo. The residue was dissolved in ethyl acetate, washed successively with 2 portions of IN hydrochloric acid, once with water, twice with a saturated sodium bicarbonate solution, and once with water. The organic layer was dried over magnesium sulfate, filtered, and concentrated in vacuo. The resulting oil was chromatographed over silica gel eluting with 60:40 ethyl acetate/hexane. The appropriate fractions were combined and concentrated in vacuo providing a white solid. The residue was triturated with diethyl ether to provide 975 mg of the desired title intermediate.

m/e: M++1=638.

IR (CDCl3): 1774 cm$^{-1}$ (β-lactam carbonyl)

NMR (CDCl3): 1.83-2.00 (1H, m), 2.18-2.30 (IH, m), 2.62-2.74 (2H, m), 4.0 (3H, s), 4.01-4.10 (1H, m), 4.64-4.84 (4H, 2d), 5.28-5.44 (4H, m), 5.62-5.68 (1H, m), 5.90-6.02 (2H, m), 7.14 (1H, s), 7.96 (1H, d), 9.50 (1H, s).

F. Preparation of 1-[7β-{[2-(allyloxycarbonyl-amino)-4-thiazolyl](methoxyimino)acetyl}amino)-2oxycarbonyl)-8-oxo-1-azabicyclo[4.2.0]oct-2-en-3-yl]pyridinium trifluoromethanesulfonate.

One gram of the 3-triflate ester named in Example IE above was dissolved in 0.8 ml of acetonitrile under a nitrogen atmosphere. To this solution was introduced 0.14 ml of pyridine. The reaction mixture was stirred under a nitrogen atmosphere for 3 days having added 0.14 ml and 0.07 ml of pyridine after 1 and 2 days, respectively. The mixture was concentrated in vacuo, redissolved in acetonitrile, and again evaporated. The residue was chromographed over silica gel eluting with a gradient of 5025:9:7:9 ethyl acetate/acetonitrile/acetic acid/water in ethyl acetate to 10025:9:7:9 ethyl acetate/acetonitrile/acetic acid/water. The desired fractions were combined, concentrated in vacuo, and then lyophilized providing 0.95 g of the desired title intermediate as a dark orange solid.

NMR (CD2Cl2): 3.96 (3H, s), 4.08-4.24 (1H, m), 4.54 (2H, d), 4.72 (2H, d), 5.04-6.20 (7H, m), 7.20 (1H, s), 7.92-8.20 (2H, m), 8.32-8.60 (1H, m), 9.12-9.36 (2H, m).

EXAMPLES 2-10

The following intermediates were prepared according to the procedure of Example 1F from the intermediate of Example lE or related intermediate and the corresponding pyridine or imidazole derivative.

2. 6-[7β-({[2-(allyloxycarbonyl)amino-4thiazolyl](methoxyimino)acetyl}amino-2-(allyloxycarbonyl)- 0 8-oxo-1-azabicyclo[4.2.0]oct-2-en-3-yl]-2-(4-methoxyphenyl)thieno[2,3-c]pyridinium trifluoromethanesulfonate, 35yield.

NMR (CDCl3): 3.84 (6H, s), 4.04-4.28 (1H, m), 4.36-4.76 (4H, 2d), 4.88-5.20 (9H, m), 6.88-7.06 (1H, m), 8.36-8.64 (1H, m).

3. 3-[7β-({[2-(allyloxycarbonyl)amino-4thiazolyl]-(methoxyimino)acetyl}amino)-2-(allyloxycarbonyl)8-oxo-1-azabicyclo[4.2.0]oct-2-en-3-yl]-1-methyl-1H-imidazolium trifluoromethanesulfonate, 77yield.

NMR (DMSO): 1.73-1.93 (1H, m), 2.10-2.23 (1H, m), 2.50-2.77 (1H, m), 2.80-2.97 (1H, m), 3.87 (3H, s), 3.89 (3H, s), 3.93-4.13 (1H, m), 4.53-4.70 (4H, m), 5.13-5.50 (4H, m), 5.63-5.83 (2H, m), 5.87-6.03 (1H, m), 7.37 (1H, s), 7.83 (1H, s), 7.97 (1H, s), 9.35 (1H, s), 9.52 (2H, d).

4. 5-[7β-({[2-(allyloxycarbonyl)amino-4thiazolyl]-(methoxyim;ino)acetyl}amino)-2-(allyloxycarbonyl)8-oxo-1-azabicyclo[4.2.0]oct-2-en-3-yl]-3-methyl-3H-imidazo[4,5-c]pyridin-5-ium trifluoromethanesulfonate, 71yield.

NMR (CD3CN): 2.05-2.41 (2H, m), 3.89 (3H, s), 4.01 (3H, s), 4.05-4.27 (1H, m), 4.43 (2H, d), 4.63 (2H, d), 4.89-6.13 (8H, m), 7.13 (1H, s), 8.01 (1H, d), 8.43 (1H, d), 8.57 (1H, s).

5. 1-[7β-({[2-(allyloxycarbonyl)amino-4thiazolyl]-(methoxyimino)acetyl}amino)-2-(allyloxycarbonyl)- 0 8-oxo-1-azabicyclo[4.2.0]oct-2-en-3-yl]-6,7-dihydro-5H1-pyrindinium trifluoromethanesulfonate, 75yield.

NMR (CD3CN): 2.00-2.32 (4H, m), 2.68-3.00 (2H, m), 3.04-3.50 (4H, m), 3.92 (3H, s), 4.04-4.28 (1H, m), 4.62 (2H, d), 4.66 (2H, d), 5.04-5.32 (4H, m), 5.38-5.68 (2H, m), 5.72-6.04 (1H, m), 7.28 (1H, s), 7.40-7.82 (2H, m}, 8.16-8.32 (2H, m).

6. 1-[7β-({[2-(allyloxycarbonyl)amino-4- 0 thiazolyl]-(methoxyim:noi)acetyl}amino)-2-(allyloxycarbonyl)8-oxo-1-azabicyclo[4.2.0]oct-2-en-3-yl]-5,6,7,8-tetrahydroquinolinium trifluoromethanesulfonate, 65yield. NMR.

7. 1-[7β-({[2-(allyloxycarbonyl)amino-4thiazolyl]-(methoxyimino)acetyl}amino)-2-(allyloxycarbonyl)8-oxo-1-azabicyclo[4.2.0]oct-2-en-3-yl]-2,5-dimethylpyridinium trifluoromethanesulfonate, 65yield.

m/e: M++1 =595.

NMR (CD3CN): 1.87-2.93 (10H, m), 4.0 (3H, s), 4.17-4.25 (1H, m), 4.23-4.77 (4H, m), 5.17-5.47 (4H, m), 5.60-5.80 (2H, m), 5.93-6.09 (2H, m), 7.30 (1H, s), 7.58 (1H, d), 7.95 (1H, d), 8.32 (1H, d), 8.40 (1H, s), 9.43 (1H, s).

8. 1-[7β-({[2-(allyloxycarbonyl)amino-4thiazolyl]-(methoxyimino)acetyl}amino)-2-(allyloxycarbonyl)8-oxo-1-azabicyclo[4.2.0]oct-2-en-3-yl]-3,4-dimethylpyridinium trifluoromethanesulfonate, 94yield.

NMR (CD3CN): 1.87-2.33 (2H, m), 2.45 (3H, s), 2.60 (3H, s), 2.80-2.88 (2H, m), 4.00 (3H, s), 4.13-4.23 (1H, m), 4.27-4.60 (2H, m), 4.75 (2H, d), 5.17-5.47 (4H, m), 5.63-5.77 (2H, m), 5.95-6.07 (1H, m), 7.30 (1H, s), 7.72 (1H, d), 7.85 (1H, d), 8.40-8.90 (2H, m), 9.30-9.60 (1H, s).

25 9. 1-[7β-({[2-t-butoxycarbonyl)amino-4thiazolyl]-(methoxyimino)acetyl}amino)-2-(diphenyl-methoxycabbonyl)-8-oxo-1-azabicyclo[4.2.0]oct-2-en3-yl]-4-(dimethylamino)pyridinium trifluoromethanesulfonate, 81% yield.

NMR (CD3CN): 1.47 (9H, s), 2.67 (2H, m), 3.07 (6H, s), 3.97 (3H, s), 4.03-4.13 (1H, m), 5.60-5.67 (1H, m), 6.58 (2H, d), 6.70 (1H, s), 7.13-7.40 (10H, m), 7.62 (1H, d), 7.78 (2H, d), 9.20 (1H, s).

10. 1-[7β-({[2-(triphenylmethyl)amino-4thiazolyl]-(benzyloxyimino)acetyl}amino)-2-(diphenyl-methoxycarbonyl)-8-oxo-1-azabicyclo[4.2.0]oct-2-en3-yl]-3,4-dimethylpyridinium trifluoromethanesulfonate, 81yield.

NMR (CD3CN): 1.62-1.83 (2H, m), 2.25 (3H, s), 2.40 (3H, s), 2.53-2.64 (2H, m), 3.96-4.07 (1H, m), 5.14 (2H, s), 5.45-5.58 (1H, m), 6.60 (1H, s), 6.73 (1H, s), 7.10-7.60 (33H, m), 8.28-8.38 (2H, m).

EXAMPLE 11

1-(7β-{[(2-amino-4-thiazolyl)(methoxyimino)acetyl]amino}2-carboxy-8-oxo-1-azabicyclo[hydroxide, inner salt To a solution of 22 mg of triphenylphosphine and 4.1 mg of palladium acetate in 10.5 ml of acetonitrile were added 300 mg of the diallyl protected intermediate of Example 1F under a nitrogen atmosphere. After solution was complete, 2.0 ml of diethyl ether were added and the mixture cooled by means of an external ice bath. In dropwise fashion, 231 mcl of tributyl tin hydride were added. After 15 minutes, the ice bath was removed and the reaction mixture allowed to warm to room temperature. After 30 minutes, the ice bath was again applied and 0.88 ml of 1N hydrochloric acid added. After stirring for 10 minutes, the ice bath was removed and the reaction mixture stirred an additional 20 minutes. Diethyl ether and water were added and the layers were separated. The separated water layer was washed 3 times with diethyl ether/hexane. The water layer was then applied to a HP 20-SS column packed with water. Using a continuous gradient of 800 ml of water and 800 ml of 10acetonitrile in water, the desired product was eluted and appropriate fractions combined and lyophilized providing 36 mg of the desired title product.

IR: 1768.2 cm$^{-1}$.

NMR (DMSO, 500 MHz): 1.85-1.93 (1H, m), 2.00-2.08 (1H, m), 2.65-2.73 (1H, m), 2.74-2.80 (1H, m), 3.87 (3H, s), 3.88-3.93 (1H, m), 5.43-5.42 (1H, m), 6.80 (1H, s), 7.23 (2H, s), 8.12 (2H, triplet), 8.60 (1H, triplet), 8.98 (2H, d), 9.39 (1H, d).

MS: M$^+$+1 =443.

EXAMPLES 12-18

Employing the same procedure as taught above for Example 11 except that tetrahydrofuran was used in place of diethyl ether, the following compounds were prepared from the corresponding di-protected intermediates of Examples 2-8.

12. 6-(7β-{[(2-amino-4-thiazolyl)(methoxyimino)acetyl]amino}-2-carboxy-8-oxo-1-azabicyclo[4.2.0]-oct-2-en-3-yl)-2-(4-methoxyphenyl)thieno[-hydroxide, inner salt, 10yield, m.p. =210°-211° C.

MS: M$^+$+1 =605.

13. 3-(7β-{[(2-amino-4-thiazolyl)(methoxyimino)acetyl]amino}-2-carboxy-8-oxo-1-azabicyclo4.2.0]- oct-2-en-3-yl)-1-methyl-1H-imidazolium hydroxide, inn salt, 34yield.

MS: M$^+$+1 =446.

IR: 1765.3 cm$^{-1}$.

NMR (DMSO): 1.70-2.00 (2H, m), 2.49-2.63 (2H, m), 3.77-3.87 (4H, m), 5.35-5.43 (1H, q), 6.77 (1H, s), 7.20 (1H, s), 7.68 (1H, s), 7.80 (1H, s), 9.15 (1H, s), 9.33 (1H, d).

14. 5-(7-{[(2-amino-4-thiazolyl)(methoxyimino)acetyl]amino}-2-carboxy-8-oxo-1-azabicyclo[4.2.0]-oct-2-en-3-yl)-3-methyl-3H-imidazol[4,5 hydroxide, inner salt, 23yield, m.p. =219-220° C.

MS: M$^+$+1 =497.

IR: 1766.5 cm$^{-1}$.

NMR (DMSO): 1.74-2.26 (2H, m), 2.74-2.90 (4H, m), 3.02 (1H, s), 5.32-5.50 (1H, m), 6.74 (1H, s), 7.14 (1H, s), 8.16 (1H, d), 8.50 (H, d), 8.54 (1H, s), 9.32 (1H, d), 9.66 (1H, s).

15. 1-(7-{[(2-amino-4-thiazolyl)(methoxyimino)acetyl]amino}-2-.carboxy-8-oxo-1-azabicyclo[4.2.0]-oct-2-en-3-yl)-6,7-dihydro-5H-1-pyrind inner salt, 57yield.

MS: M$^+$+1 =483.

IR: 1765 cm$^{-1}$

NMR (DMSO): 1.80-2.27 (4H, m), 2.43-2.72 (2H,m), 3.07-3.40 (4H, m), 3.83 (3H, s), 5.40-5.50 (1H, m), 6.77 (1H, s), 7.20 (2H, s), 7.77-7.87 (1H, q), 8.37-8.43 (1H, m), 8.55-8.73 (1H, 2d), 9.30-9.40 (1H, 2d).

16. 1-(7β-{[(2-amino-4-thiazolyl)(methoxyimino)acetyl]amino}-2-carboxy-8-oxo-1-azabicyclo[4.2.0]oct-2-en-3-yl)-5,6,7,8-tetrahydroquinolinium hydroxide, inner salt, 56yield, m.p. =220-223° C.

MS: M$^+$+1 =497.

IR: 1769.4 cm$^{-1}$.

17. 1-(7β-{[(2-amino-4-thiazolyl)(methoxyimino)acetyl]amino}-2-carboxy-8-oxo-1-azabicyclo[4.2.0]-oct-2-en-3-yl)-2,5-dimethylpyridinium hydroxide, in salt, 31yield.

MS: M$^+$+1 =471.

NMR (DMSO): 1.83-2.17 (2H, m), 2.40-2.43 (3H, 2s), 2.63-2.68 (3H, 2s), 2.73-2.80 (2H, m), 4.88 (3H, s), 4.03-4.20 (2H, m), 5.55-5.73 (1H, 2 quartets), 6.80 (1H, s), 7.20 (2H, s), 7.80-7.97 (1H, m), 8.28-8.47 (1H, 2d), 8.70-8.80 (1H, 2s), 9.30-9.53 (1H, 2d).

18. 1-(7β-{[(2-amino-4-thiazolyl)(methoxyimino)acetyl]amino}--.carboxy-8-oxo-1-azabicyclo4.2.0]-oct-2-en-3-yl)-3,4-dimethylpyridinium hydroxide, inner salt, 47yield.

MS: M$^+$+1 =471.

IR: 1772.5 cm$^{-1}$.

NMR (DMSO): 1.73-2.07 (2H, m), 2.35-2.77 (8H, m), 3.77-3.90 (4H, m), 5.38-5.43 (1H, m), 6.77 (1H, s), 7.20 (1H, s), 7.87 (1 H, d), 8.63 (1H, d), 8.77 (1H, s), 9.38, (1H, d).

EXAMPLE 19 1-(2-{[(4-nitrophenyl)methoxy]carbonyl}-8-oxo-7-[(phenoxyacetyl)amino]-1-azabicyclo4.2.0trifluoromethanesulfonate The title product was prepared from p-nitrobenzyl 7β-phenoxyacetylamino-3-trifluoromethanesulfonyloxy-1-carba(dethia)-3-cephem-4-carboxylate in 94yield according to the procedure of Example 1F. MS.

EXAMPLE 20

1-(7β-{[(2-amino-4-thiazolyl)(methoxyimino)acetyl]amino}-2-carboxy-8-oxo-1-azabicyclo[-(dimethylamino)pyridinium hydroxide, inner s To 175 mg of the intermediate of Example 9 was added a 0° C. mixture of 1.2 ml of trifluoroacetic acid, 90 mcl of triethylsilane, and 1.2 ml of methylene chloride. After stirring at 0° C for 30 minutes, the external cooling bath was removed for five minutes and diethyl ether added to precipitate the product. The solid was recovered by centrifugation, washed three times with diethyl ether, and dried to provide 81 mg of crude title product. The material was dissolved in a small amount of water, filtered, and chromatographed by reverse phase HPLC employing 8acetonitrile and 1acetic acid in water as the eluant. Lyophilization of the desired fractions provided 41 mg of the desired title product.

NMR (DMSO): 1.70–2.00 (2H, m), 2.38–2.66 (2H,m), 3.20 (6H,s), 3.70–3.86 (2H,m), 5.30–5.37 (1H, m), 6.73 (1H, s), 6.95 (2H, d), 7.68 (2H, s), 8.10 (2H, d), 9.33 (1H, d).

EXAMPLE 21

1-(7β-{[(2-amino-4-thiazolyl)(benzyloxyimino)acetyl-]amino}-2-carboxy-8-oxo-1-azabicy-dimethylpyridinium hydroxide, inner salt Fifty milligrams of the intermediate from Example 10 were added to 0.3 ml of trifluoroacetic acid and 9.7 ml of thiophenol under a nitrogen atmosphere and cooled by means of an external ethanol/ice bath. After stirring for 30 minutes at 0° C and 10 minutes with the ice bath removed, diethyl ether was added and the solid worked up in the same manner as in Example 21 above. Chromatography eluting with a continuous gradient of water to 12acetonitrile in water and lyophilization provided 12 mg of the desired title product.

NMR (DMSO): 1.72–2.01 (2H, m), 2.45 (3H, s), 2.61 (3H, s), 2.72–2.88 (2H, m), 3.98–4.08 (1H, m), 5.18 (2H, s), 5.64–5.76 (1H, m), 6.84 (1H, s), 7.24–7.36 (7H, m), 8.08 (1H, d), 7.94 (1H, d), 9.00 (1H, s), 9.56 (1H, d).

The 1-carbacephalosporins provided herein inhibit the growth of microorganisms pathogenic to man and animals. The compounds are broad spectrum antibiotics which are particularly effective against grampositive bacteria.

This invention also provides a method for treating infectious diseases in man and animals and pharmaceutical formulations suitable for administration in the treatment method. The therapeutic method of this invention comprises administering to a man or animal an antibiotically effective non-toxic dose of a compound represented by the formula I wherein $R_a$ is a negative charge, hydrogen, or a biologically labile group, or a solvate or pharmaceutically acceptable salt thereof.

An antibiotically effective amount is usually an amount between about 25 mg and about 2 grams. The compound, salt or ester may be administered in a single dose or in multiple doses throughout the day. Treatment may continue for a week to ten days or longer depending upon the duration of the infection. The particular dose and regimen can depend on such factors as the weight and age of the patient, th.e particular causative organism, the severity of the infection, the general health of the patient, and the tolerance of the individual to the antibiotic.

The 1-carbacephalosporins may be administered parenterally, orally, subcutaneously or rectally. As with other β-lactam antibiotics, the method of this invention may be used prophylactically to prevent infections after exposure or before possible exposure e.g., preoperatively. The antibiotic 1-carbacephalosporins may be administered by conventional methods e.g., in capsules, tablets, by syringe, or by intravenous drip.

The pharmaceutical formulations of the invention comprise an antibiotically effective non-toxic amount of a 1-carbacephalosporin represented by the formula I wherein $R_a$ is a negative charge, hydrogen, or a biologically labile group, or a solvate or pharmaceutically acceptable salt thereof, and a pharmaceutical carrier.

Formulations for oral administration include capsules, tablets, lozenges, and liquid suspensions. The antibiotic or a salt or ester thereof in the form of a dry powder is encapsulated in gelatin capsules for oral use. The antibiotic may also be blended with an excipient, e.g., a stabilizer, prior to filling. Capsules may contain between about 100 mg and about 500 mg to provide unit dosage formulations.

Tablets containing between about 100 mg and 500 mg of the antibiotic or a salt or ester thereof are formulated by conventional means and may contain in addition a binding agent, disintegrating agent, stabilizing agent, antioxidant, etc.

Liquid preparations of the antibiotic may be prepared for infant and geriatric use. Pediatric suspensions are formulated with the antibiotic oral excipients such as suspending agents, flavoring agents, stabilizers, and the like. Solutions of the antibiotics likewise may be formulated with solubilizing agents, flavoring agents, sugar, water, etc.

Parenteral formulations of the antibiotics for injection are formulated with Water-for-Injection, Ringer's solution, physiological saline, or glucose solution. The antibiotic also may be administered in an intravenous fluid by the drip method.

For parenteral use, the antibiotic, a salt, solvate, or biologically labile ester thereof, is made up preferably in dry crystalline powder form or as a lyophilized powder and filled into vials. Such vials contain between about 100 mg and about 2 grams of antibiotic per vial.

We claim:

1. A compound of the formula

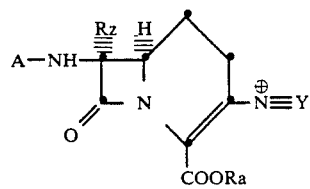

wherein A is hydrogen or an acyl group

wherein R is hydrogen, $C_1$–$C_6$ alkyl, $C_1$–$C_6$ alkyl substituted by cyano, carboxy, halogen, amino, $C_1$–$C_4$ alkoxy, $C_1$–$C_4$ alkylthio, trifluoromethyl, or trifluoromethylthio, naphthyl, an optionally substituted phenyl group represented by the formula

wherein a and a' independently are hydrogen, halogen, hydroxy, $C_1$–$C_4$ alkoxy, $C_1$–$C_4$ alkanoyloxy, $C_1$–$C_4$ l alkyl, $C_1$–$C_4$ alkylthio, amino, $C_1$–$C_4$ alkanoylamino, $C_1$–$C_4$ alkylsulfonylamino, carboxy, carbamoyl, hydroxymethyl, aminomethyl, or carboxymethyl;

a group represented by the formula

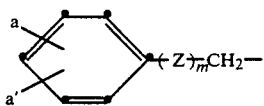

wherein a and a' have the same meanings as defined above, Z is O or S, and m is 0 or 1;
a heteroarylmethyl group represented by the formula

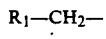

wherein $R_1$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_1$-$C_4$ alkyl, $C_1$-$C_4$ alkoxy, $C_1$-$C_4$ alkylsulfonylamino;
a substituted methyl group represented by the formula

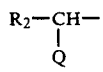

wherein $R_2$ is cyclohexa-1,4-dienyl, or an optionally substituted phenyl group represented by the formula

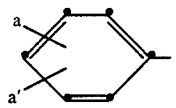

wherein a and a' have the above defined meanings, or $R_2$ is $R_1$ as defined above, and Q is hydroxy, $C_1$-$C_4$ alkanoyloxy, carboxy, sulfo, amino, or a substituted amino group represented by the formula

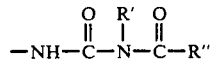

wherein R" is $C_1$-$C_4$ alkyl, furyl, thienyl, phenyl, halophenyl, nitrophenyl, styryl, halostyryl or a group

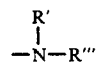

wherein each R' is independently hydrogen or $C_1$-$C_3$ alkyl, and R''' is hydrogen, $C_1$-$C_3$ alkylsulfonyl, $C_1$-$C_3$ alkyl, or $C_1$-$C_4$ alkanoyl; or Q is a substituted amino group represented by the formula

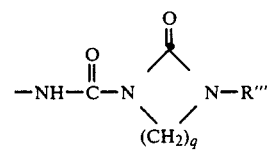

wherein R''' has the same meaning as defined above and q is 2 or 3;
or Q is a substituted amino group represented by the formula

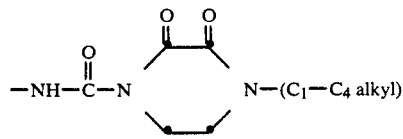

or a benzamido gorup represented by the formula

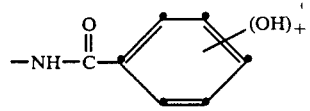

wherein t is 1 to 3;
a pyridone gorup

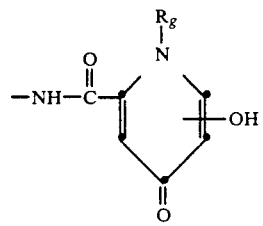

a pyridyl group

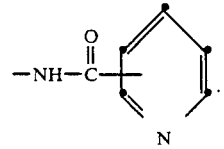

or said pyridyl group substituted by $C_1$-$C_4$ alkyl, amino, carboxy, hydroxy or halogen; and imidazolyl or pyrazolyl group

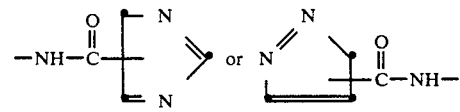

or said imidazolyl or pyrazolyl rings substituted by $C_1$-$C_4$ alkyl, carboxy, amino, or halogen;
a benzpyridazin-4-one group or tautomer thereof

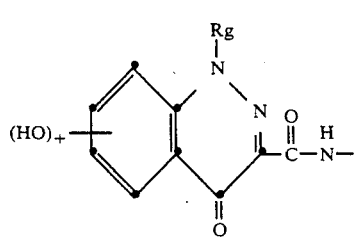

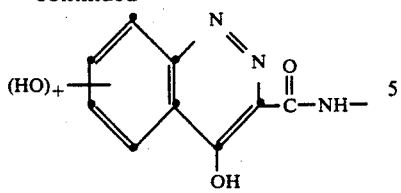

wherein rg is hydrogen or $C_1$–$C_3$ alkyl, and t is 1 to 3; or a benzpyranone group

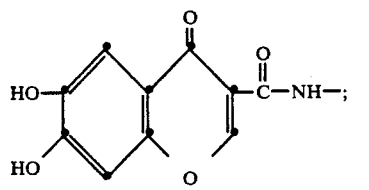

or R is a keto group or an oximino-substituted group represented by the formulae

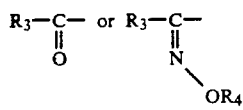

wherein $R_3$ is $R_1$ or $R_2$ as defined above and $R_4$ is hydrogen, $C_1$–$C_4$ alkyl, or a group represented by the formula

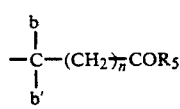

wherein b and b' independently are hydrogen or $C_1$–$C_3$ alkyl, or b and b', when taken together with the carbon to which they are bonded, form a 3-to 6-membered carbocyclic ring, n is 0–3, and $R_5$ is hydroxy, $C_1$–$C_4$ alkoxy, amino, $C_1$–$C_4$ alkylamino, or di ($C_1$–$C_4$ alkyl) amino;

$R_a$ is a negative charge;

$R_z$ is hydrogen, $C_1$–$C_4$ alkoxy, $C_1$–$C_4$ alkylthio, or a formamido group, —NHCHO;

—N⊕≡Y is a) a pyridinium ring, whicy may be substituted with one or two of the following substituents: $C_1$ to $C_6$ alkyl, $C_1$ to $C_6$ substituted alkyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, halo, cyano, hydroxy, protected hydroxy, $C_1$ to $C_4$ alkoxy, $C_1$ to $C_4$ alkylthio, $C_1$ $C_4$ alkylsulfoxide, $C_1$ to $C_4$ alkylsulfonyl, phenyl, substituted phenyl, formyl, $C_2$ to $C_4$ alkanoyl, benzyl, benzoyl, amino, protected amino, $C_1$ to $C_4$ alkylamino, di($C_1$ to $C_4$ alkyl)amino, trifluoromethyl, carboxy, protected carboxy, $C_1$ to $C_4$ alkoxycarbonyl, aminomethyl, protected aminomethyl, carboxymethy, protected carboxymethyl, carbamoyl, which may be substituted once or twice with a $C_1$ to $C_6$ alkyl group, an aminosulfonyl group (which may be substituted once or twice with a $C_1$ to $C_6$ alkyl group), or a sulfonic acid;

b) a quinolinium, isoquinolinium, (1 to 2)-pyradizinium, (1or 3)-pyrimidinium, $N^3$-($C_1$–$C_4$ alkyl)-imidazolinium, pyridazinium, phthalazinium, quinazolinium, purinium, pyrazinium, thiazolinium, isothiazolinium, oxazolinium, isoxazolinium, (3 or 4)-1,3,4-thiadiazolinium, (2 or 4)-1,2,4-thiadia-zolinium, (2 or 5)-1,2,5-thiadiazolinium, (3 or 4)-1,3,4-oxadiazolinium, (2 or 4)-1,2,4-oxadia-zolinium, or a (2 or 5)-1,2,5-oxadiazolinium ring, or the mono or di-substituted derivatives thereof, wherein the substitutents can be the same or different (and in the case of the quinolinium or isoquinolinium rings, on one or both rings) and are amino, protected amino, $C_1$ to $C_4$ alkylamino, di($C_1$ to $C_4$ alkyl)amino, hydroxy, protected hydroxy, $C_1$ to $C_4$ alkoxy, $C_1$ to $C_4$ alkylthio, $C_1$ to $C_4$ alkylsulfoxide, $C_1$ to $C_4$ alkylsulfonyl, cyano, halo, $C_1$ to $C_6$ alkyl, $C_1$ to $C_6$ substituted alkyl, trifluoromethyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, sulfonic acid, carboxy, protected carboxy, $C_1$ to $C_4$ alkoxy-carbonyl, hydroxy-($C_1$ to $C_3$ alkyl), protected hydroxy-($C_1$ to $C_3$ alkyl), formyl, $C_2$ to $C_4$ alkanoyl, an aminosulfonyl group (which may be substituted once or twice with a $C_1$ to $C_6$ alkyl group), carbamoyl (which may be substituted once or twice with a $C_1$ to $C_6$ alkyl group), amino-methyl, protected aminomethyl, carboxymethyl, (protected carboxy)-methyl, phenyl, substituted phenyl, benzoyl or benzyl;

c) a gorup of the formula

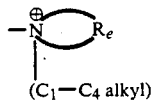

wherein $R_e$ together with the nitrogen atom to which it is attached form a saturated or partially unsaturated 4 to 10 membered heterocyclic ring which may contain one sulfur or one oxygen and one or more nitrogen atoms and whereinthe substitutent may be $C_1$ to $C_6$ alkyl, $C_1$ to $C_6$ substituted cycloalkyl, $C_5$ to $C_7$ cycloalkenyl, $C_5$ to $C_7$ substituted cycloalkenyl, halo, cyano, hydroxy, protected hydroxy, $C_1$ to $C_4$ alkoxy, $C_1$ to $C_4$ alkylthio, $C_1$ to $C_4$ alkylsulfoxide, $C_1$ to $C_4$ alkylsulfonyl, phenyl, substituted phenyl, formyl, $C_2$ to $C_4$ alkanoyl, benzyl, benzoyl, amino, protected amino $C_1$ to $C_4$ alkylamino, di($C_1$ to $C_4$ alkyl)amino, trifluoromethyl, arboxy, protected carboxy, $C_1$ to $C_4$ alkoxycarbonyl, aminomethyl, protected aminomethyl, carboxymethyl, protected carboxy-methyl, carbamoyl (which may be substituted once or twice with a $C_1$ to $C_6$ alkyl group), amino-sulfonyl (which may be substituted once or twice with a $C_1$ to $C_6$ alkyl group), or sulfonic acid, or the benzo-fused analogs of the substituted or unsubstituted, saturated or partially unsaturated ring, or —N⊕≡Y is tri($C_1$–$C_4$ alkyl)ammonium;

and pharmaceutically acceptable salts thereof.

2. A compound of claim 1 wherein R is

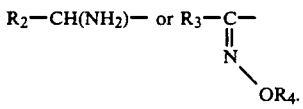

3. A compound of claim 2 wherein —N⊕≡Y is substituted or unsubstituted pyridinium, quinolinium, isoquinolinium, 1- or 2-pyridazinium, 1- or 3-pyrimidinium, pyrazinium, thiazolinium, isothiazolinium, oxazolinium, isoxazolinium, 1,2,4-, 1,2,5-, or 1,3,4-thiadiazolinium or -oxadiazolinium, or a group of the formula

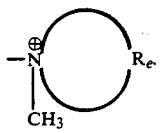

4. A compound of claim 3 wherein RCO- is D-phenylglycyl, D-4-hydroxphenylglycl, D-2-thienyglycl, D-benzothien-3-ylglcyl, (2-aminothiazol-4-yl)-(methoxyimino)acetyl, or (2-aminooxazol-4-ys)-methoxyimino)acetyl.

5. The compound of claim 4 wherein —N⊕≡Y is pyridinium, $R_z$ is hydrogen, and A is (2-amino-4-thiazolyl)-(methoximino) acetyl, or a pharmaceutically acceptable salt thereof.

6. The compound of claim 2 wherein A is (2-amino-4-thiazolyl)(methoxyimino)acetyl, —N⊕≡Y is 4-methoxyphenyl) thieno[2,3-c]pyridinium, and $R_Z$ is hydrogen, or a pharmaceutically acceptable non-toxic salt thereof.

7. The compound of claim 2 wherein A is (1-amino-4-thiazolyl)(methoxyimino)acetyl;—N⊕≡is 1-methyl-1H-imidaxolim, and $R_Z$ is hydrogen or a pharmaceutically acceptable non-toxic salt thereof.

8. The compound of claim 2 wherein A is (2-amino-4-thiazolyl)(methoxyimino)acetyl;—N⊕≡Y is 3-methyl-3H-imidazol[4,5-c]pyridin-5-ium, and $R_Z$is hydrogen, or a pharmaceutically acceptable non-toxic salt thereof.

9. The compound of claim 2 wherein A is (2-amino-4-thiazolyl)(methoxyimino)acetyl; —N⊕≡is 6,7-dihydro-5H-1-pyrindinium, and $R_Z$is hydrogen, or a pharmaceutically acceptable non-toxic salt thereof.

10. The compound of claim 2 wherein A is (2-amino-4-thiazolyl)(methoxyimino)acety; —N⊕≡Y is 5,6,7,8-tetrahydroquinoliim; and $R_Z$ is hydrogen, or a pharmaceutically acceptable non-toxic salt thereof.

11. The compound of claim 4 wherien A is (2-amino-4-thiazolyl)(methoxyimino)acety; —⊕≡Y is 5,6,7,8-tetrahydroquinolium, and $R_{Z\ pl}$ is hydrogen, or a pharmaceutically acceptable non-toxic salt thereof.

12. The compound of claim 4 wherein A is (2-amino-4-thiazolyl)(methoxyimino)acetyl, —⊕≡Y is 3,4-dimethylpyridinium, and $R_Z$ is hydrogen or a pharmaceutically acceptable non-toxic salt thereof.

13. The compound of claim 5 wherein A is (2-amino-4-thiazolyl)(methoxyimino)acetyl;—⊕≡Y is 4-(dimethylamino)pyridinium, and $R_Z$is hydrogen or a pharmaceutically acceptable non-toxic salt thereof.

14. The compound of claim 3 wherein A is (2-amino-4-thiazolyl)(benzyloxyimino)acetyl; —⊕≡Y is 3,4-dimethylpyridinium, and $R_Z$ is hydrogen, or a pharmaceutically acceptable non-toxic salt thereof.

15. A pharmaceutical formulation comprising a antibiotically effective amount of a compound of claim 1 or a pharmaceutically acceptable salt thereof and a pharmaceutical carrier.

16. A pharmaceutical formulationcomprising a antibiotically effective amount of a compound of claim 2 and a pharmaceutical carrier.

17. A method for treating bacterial infections in man and other animals which comprises administrating an antibacterially effective amount of an antibiotic compound of claim 1 or a pharmaceutically acceptable salt thereof.

18. A method for treating bacterial infections in man and other animals which comprises administrating an antibacterially effective amount of an antibiotic compound of claim 2 or a pharmaceutically acceptable salt thereof.

* * * * *

UNITED STATES PATENT AND TRADEMARK OFFICE
CERTIFICATE OF CORRECTION

PATENT NO. : 5,019,571

DATED : May 28, 1991

INVENTOR(S) : Gwendolyn K. Cook and John H. McDonald, III

Page 1 of 2

It is certified that error appears in the above-identified patent and that said Letters Patent is hereby corrected as shown below:

Column 30, line 64, "1 alkyl" should read -- alkyl --.

Column 32, line 19, "gorup" should read -- group --.

Column 36, line 11, "wherien" should read --wherein--.

Column 33, line 10, "rg" should read -- $R_g$ --.

Column 34, line 33, "gorup" should read -- group --.

Column 35, line 34, "4" should read -- (4 --.

Column 35, line 38, "1" should read -- 2 --.

Column 35, line 40, "≡ is" should read -- ≡ Y is --.

UNITED STATES PATENT AND TRADEMARK OFFICE
CERTIFICATE OF CORRECTION

PATENT NO. : 5,019,571

DATED : May 28, 1991

INVENTOR(S) : Gwendolyn K. Cook and John H. McDonald, III

It is certified that error appears in the above-identified patent and that said Letters Patent is hereby corrected as shown below:

Column 36, line 4, "≡ is" should read -- ≡ Y is --.

Column 36, line 12, "; -" should read -- ; -N --.

Column 36, lines 13-14, "p1 is hydrogen, or a pharmaceutically acceptable non-toxic salt thereof" should read -- is hydrogen, or a pharmaceutically acceptable non-toxic salt thereof --.

Column 36, line 16, ", --" should read --, -N--.

Column 36, line 20, ";-" should read -- ; -N --.

Column 36, line 24, "; -" should read -- ; -N --.

Signed and Sealed this

Twenty-second Day of December, 1992

Attest:

DOUGLAS B. COMER

*Attesting Officer*  *Acting Commissioner of Patents and Trademarks*